United States Patent
Wallace

(10) Patent No.: US 9,134,212 B2
(45) Date of Patent: Sep. 15, 2015

(54) MODAL IMPACT TESTING ASSEMBLY, SYSTEM AND METHOD

(71) Applicant: The Boeing Company, Chicago, IL (US)

(72) Inventor: Steven G. Wallace, University Place, WA (US)

(73) Assignee: The Boeing Company, Chicago, IL (US)

( * ) Notice: Subject to any disclaimer, the term of this patent is extended or adjusted under 35 U.S.C. 154(b) by 168 days.

(21) Appl. No.: 13/937,204

(22) Filed: Jul. 8, 2013

(65) Prior Publication Data

US 2015/0007634 A1    Jan. 8, 2015

(51) Int. Cl.
| | |
|---|---|
| *G01N 3/30* | (2006.01) |
| *G01M 7/08* | (2006.01) |
| *G01M 1/20* | (2006.01) |
| *G01N 3/34* | (2006.01) |
| *G01M 1/16* | (2006.01) |
| *G01M 1/22* | (2006.01) |

(52) U.S. Cl.
CPC . *G01N 3/30* (2013.01); *G01M 7/08* (2013.01); *G01M 1/16* (2013.01); *G01M 1/20* (2013.01); *G01M 1/225* (2013.01); *G01N 3/34* (2013.01)

(58) Field of Classification Search
CPC ............ G01N 3/34; G01M 7/08; G01M 1/16; G01M 1/20; G01M 1/225
USPC ......................................... 73/12.09, 658–660
See application file for complete search history.

(56) References Cited

U.S. PATENT DOCUMENTS

| | | | | |
|---|---|---|---|---|
| 4,111,488 | A * | 9/1978 | Sigott et al. ...................... | 299/10 |
| 4,448,077 | A * | 5/1984 | Sato et al. ....................... | 73/660 |
| 4,607,529 | A * | 8/1986 | Morey ............................ | 73/660 |
| 4,850,099 | A | 7/1989 | Scollard | |
| 6,347,542 | B1 * | 2/2002 | Larsson et al. ................ | 73/12.12 |
| 6,415,661 | B1 * | 7/2002 | Wiese ............................. | 73/462 |
| 6,546,781 | B1 * | 4/2003 | Deegan et al. ................. | 73/1.82 |
| 6,938,500 | B2 * | 9/2005 | Beaman et al. ............. | 73/862.49 |
| 8,830,116 | B2 * | 9/2014 | Chang et al. .................... | 342/61 |

(Continued)

FOREIGN PATENT DOCUMENTS

| | | | | |
|---|---|---|---|---|
| CN | 1477381 A | | 2/2004 | |
| DE | 10340138 A1 * | | 3/2005 | .............. G01M 7/08 |

OTHER PUBLICATIONS

Document U—Translation of DE 10340138.*

(Continued)

*Primary Examiner* — Lisa Caputo
*Assistant Examiner* — Tran M Tran

(57) ABSTRACT

There is disclosed an assembly, a system and a method for modal impart testing. The assembly has a first set of components. The first set of components include an impact assembly, a cycle control element coupled to the impact assembly, and a signal response measuring device positioned opposite the impact assembly. The assembly further has a second set of components separate from the first set of components. The second set of components include a first controller coupled to the cycle control element and a second controller coupled to the signal response measuring device. The first set of components and the second set of components form a modal impact testing assembly for modal impact testing. The impact assembly of the modal impact testing assembly is configured to impact a test element rotating at operational speeds.

25 Claims, 9 Drawing Sheets

(56) References Cited

U.S. PATENT DOCUMENTS

| | | |
|---|---|---|
| 2002/0059831 A1* | 5/2002 | Naudet et al. .................. 73/579 |
| 2011/0036172 A1* | 2/2011 | Park et al. ..................... 73/668 |
| 2014/0150526 A1* | 6/2014 | Powers et al. ............... 73/12.09 |

OTHER PUBLICATIONS

Extended European Search Report mailed Nov. 18, 2014, for counterpart EP application EP14171264.6-1557, Applicant The Boeing Company, 16 pages.

Erturk, A., et al., "Selection of design and operational parameters in spindle-holder-tool assemblies for maximum chatter stability by using a new analytical model", International Journal of Machine Tools & Manufacture, Pergamon Press, Oxford, GB, vol. 47, No. 9, Apr. 10, 2007, pp. 1401-1409, XP022025256, ISSN: 0020-7357, DOI:10.1016/J.IJMACHTOOLS.2006.08.016 (the whole document).

Ozsahin, O., et al., "Analysis and compensation of mass loading effect of accelerometers on tool point FRF measurements for chatter stability predictions", International Journal of Machine Tools & Manufacture, Elsevier, US, vol. 50, No. 6, Jun. 2, 2010, pp. 585-589, XP027016873, ISSN: 0890-6955 (the whole document).

\* cited by examiner

MODAL IMPACT TESTING ASSEMBLY, SYSTEM AND METHOD

BACKGROUND

1) Field of the Disclosure

The disclosure relates generally to modal analysis assemblies, systems and methods, and more particularly, to a modal impact testing assembly, system and method for testing a rotating element at operational speeds.

2) Description of Related Art

Modal analysis is often used to test and analyze equipment and machinery used in the manufacture of structures and component parts in the aerospace, automotive, and structural engineering and design industries, as well as other industries. Modal analysis includes modal testing of a mechanical structure, which involves acquiring, measuring and analyzing dynamic characteristics of the mechanical structure when excited by an input. For example, modal testing may be used to determine the natural mode shapes and frequencies of a mechanical structure during free vibration in order to assess the potential for structural dynamic issues, such as fatigue, vibration and noise.

A known system and method of modal testing includes modal impact testing, such as impact hammer testing. Impact hammer testing uses a hammer device with a load cell to measure the force of an impact on a test structure. Impact hammer testing has been used to perform modal impact testing of rotating elements, such as spindles, of rotating cutting machines used for machining metallic fittings or other component parts, or of other machining tool devices. Such impact hammer testing may be used to determine precise operational behavior and operating parameters of the rotating cutting machines or other machining tool devices. The impact hammer testing of the rotating elements, such as the spindles, typically involves an operator manually impacting a stationary spindle with a hand-held, impact hammer and using an accelerometer to provide a response signal.

However, in order to operate successfully at elevated speeds, certain spindles may change their bearing preload values depending on their speed of rotation. As used herein, "bearing preload value" means the amount of load placed on rolling elements or ball bearings in the spindle that enable the spindle to rotate, before the application of any external loads. Such change in bearing preload values may alter the outcome of the modal impact testing. This may, in turn, hinder the determination of accurate operational behavior and operating parameters of the rotating cutting machines or other machining tool devices undergoing modal impact testing. Previously, even with the old impact hammer testing, weeks and months of test manufacturing and production runs are needed to properly characterize static and dynamic manufacturing performance of operationally rotating spindles.

Thus, for such spindles, in order to obtain accurate operational behavior and operating parameters of the rotating cutting machines or other machining tool devices undergoing modal impact testing, a system or method of modal impact testing is needed that is performed while the spindle is rotating at operational speeds. However, manually impacting a rotating spindle requires that the operator be in close proximity to the rotating spindle and the rotating cutting machine during the modal impact testing. This may result in increased risk to the operator. Moreover, if an accelerometer is used in the modal impact testing, such accelerometer typically requires the use of connector elements, such as wires, to be connected between the accelerometer and the spindle. However, it may be difficult, if not impossible, to attach connector elements, such as wires, to a rotating spindle.

Accordingly, there is a need in the art for an improved modal impact testing assembly, system and method for modal impact testing of a rotating test element at operational speeds that provides advantages over known assemblies, systems and methods.

SUMMARY

This need for an improved modal impact testing assembly, system and method for testing a rotating element at operational speeds is satisfied with this disclosure. As discussed in the below detailed description, embodiments of the improved modal impact testing assembly, system and method for modal impact testing of a rotating test element at operational speeds may provide significant advantages over existing assemblies, systems and methods.

In an embodiment of the disclosure, there is provided an assembly for modal impact testing. The assembly comprises a first set of components. The first set of components comprise an impact assembly, a cycle control element coupled to the impact assembly, and a signal response measuring device positioned opposite the impact assembly. The assembly further comprises a second set of components separate from the first set of components. The second set of components comprise a first controller coupled to the cycle control element and a second controller coupled to the signal response measuring device. The first set of components and the second set of components comprise a modal impact testing assembly for modal impact testing, the impact assembly of the modal impact testing assembly being configured to impact a test element rotating at operational speeds.

The modal impact testing assembly may be a stationary modal impact testing assembly, and the first set of components and the test element are preferably contained within a housing structure. Alternatively, the modal impact testing assembly may be a portable modal impact testing assembly, and the first set of components are preferably substantially contained within a housing structure.

The impact assembly of the modal impact testing assembly may comprise an impact element having a load cell configured to release an impact force output when the impact element impacts the test element. The impact assembly may further comprise an elastically driven element attached to the impact element. The impact assembly may further comprise an actuating element configured to actuate the impact element and the elastically driven element so that the impact element impacts the test element.

The impact element preferably comprises an impact hammer having a tip portion configured to impact a portion of the test element. The elastically driven element preferably comprises a tuned-length leaf spring. The actuating element preferably comprises an electromagnetic solenoid.

The cycle control element preferably comprises a trigger circuit device configured to trigger the impact assembly to impact the test element. The signal response measuring device preferably comprises a laser interferometer device configured to measure a signal response when the impact assembly impacts the test element.

The first controller preferably comprises an arm trigger switch and a power element. The first controller is configured to control and power the cycle control element. The first controller is preferably coupled to the cycle control element either via a wired connection element or via a wireless connection.

The second controller preferably comprises a laser interferometer controller. The second controller is configured to control and power the signal response measuring device. The second controller is preferably coupled to the signal response measuring device either via a wired connection element or via a wireless connection.

In another embodiment of the disclosure, there is provided a system for modal impact testing. The system comprises a modal impact testing assembly. The modal impact testing assembly comprises a first set of components. The first set of components comprise an impact assembly, a cycle control element coupled to the impact assembly, and a signal response measuring device positioned opposite the impact assembly.

The modal impact testing assembly further comprises a second set of components separate from the first set of components. The second set of components comprise a first controller coupled to the cycle control element of the modal impact testing assembly. The second set of components further comprise a second controller coupled to the signal response measuring device of the modal impact testing assembly. The system further comprises a test element configured for alignment between the impact assembly and the signal response measuring device. The test element is secured to a holding element. The holding element is attached to a rotating element. The impact assembly of the modal impact testing assembly is configured to impact the test element while it is rotating at operational speeds. The system further comprises a data acquisition assembly coupled to the modal impact testing assembly. The modal impact testing assembly, the test element, and the data acquisition assembly together comprise a modal impact testing system for modal impact testing of the test element rotating at operational speeds.

The modal impact testing system may be a stationary modal impact testing system, and the first set of components and the test element are preferably contained within a housing structure. Alternatively, the modal impact testing system may be a portable modal impact testing system, and the first set of components are preferably substantially contained within a housing structure.

The impact assembly of the modal impact testing assembly of the modal impact testing system may comprise an impact element having a load cell configured to release an impact force output when the impact element impacts the test element. The impact assembly may further comprise an elastically driven element attached to the impact element. The impact assembly may further comprise an actuating element configured to actuate the impact element and the elastically driven element so that the impact element impacts the test element.

The signal response measuring device preferably comprises a laser interferometer device configured to measure a signal response when the impact assembly impacts the test element. The first controller preferably comprises an arm trigger switch and a power element. The second controller preferably comprises a laser interferometer controller. The first controller and the second controller are preferably coupled to the modal impact testing assembly either via a wired connection element or via a wireless connection.

The data acquisition assembly preferably comprises one or more of a signal analyzer, a computer, a computer processor, and a power supply. The power supply may preferably comprise an integrated electronics piezoelectric power supply. The data acquisition assembly is preferably coupled to the modal impact testing assembly either via one or more signal cable connection elements or via a wireless connection.

In another embodiment of the disclosure, there is provided a method for modal impact testing. The method comprises the step of securing a test element to a holding element and attaching the holding element to a rotating element. The method further comprises the step of positioning the test element in relation to a modal impact testing assembly by aligning the test element between an impact assembly and a signal response measuring device of the modal impact testing assembly. The method further comprises the step of coupling a first controller to a cycle control element of the modal impact testing assembly.

The method further comprises the step of coupling a second controller to the signal response measuring device of the modal impact testing assembly. The method further comprises the step of coupling a data acquisition assembly to the first controller and to the second controller. The method further comprises the step of rotating the test element to determine an initial rotational speed. The method further comprises the step of arming the first controller. The method further comprises the step of triggering the first controller to initiate modal impact testing of the rotating test element. The method further comprises the step of obtaining with the data acquisition assembly, data at different rotational speeds of the rotating test element.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and will fully convey the scope of the disclosure to those skilled in the art.

Figure 1:
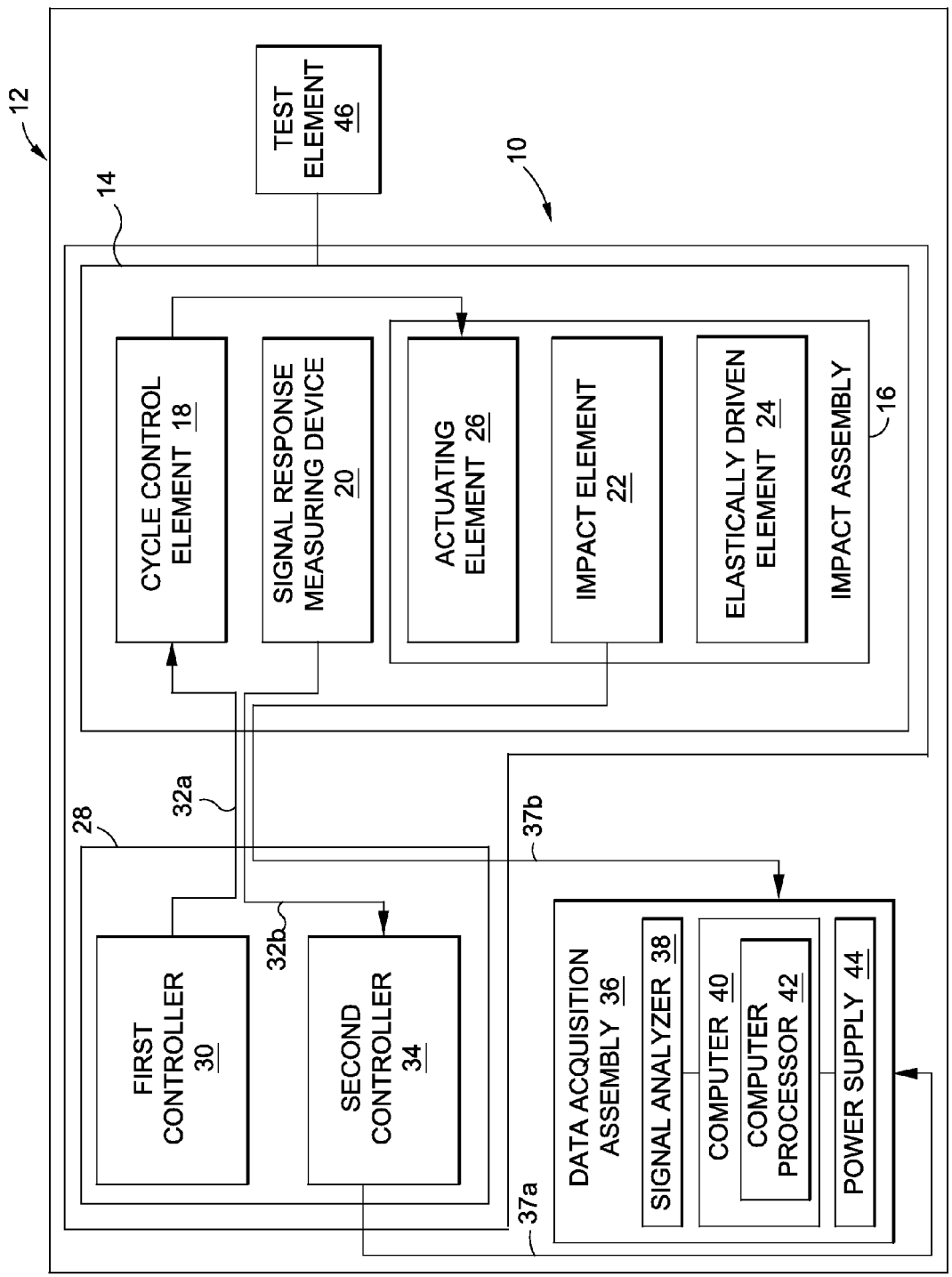
FIG. 1 is an illustration of a block diagram illustrating an embodiment of a modal impact testing assembly and an embodiment of a modal impact testing system of the disclosure.

Now referring to the Figures, FIG. 1 is an illustration of a block diagram illustrating an embodiment of a modal impact testing assembly 10 and an embodiment of a modal impact testing system 12 of the disclosure. As used herein, "modal impact testing", such as modal impact hammer testing, as performed by the modal impact testing assembly 10 and modal impact testing system 12 disclosed herein, means a form of vibration testing of a structure to be tested. Such modal impact testing may be used to determine the natural (modal) frequencies of a test element 46 (see FIGS. 1 and 2A) being tested, the modal frequencies and modal damping ratios of the test element 46 (see FIGS. 1 and 2A) being tested, or the modal frequencies, modal damping ratios, and mode shapes of the test element 46 (see FIGS. 1 and 2A) being tested. The duration of the impact time is directly linked to the frequency content of the force applied.

The teachings of the disclosed embodiments of the modal impact testing assembly 10 (see FIGS. 1 and 2A), modal impact testing system 12 (see FIGS. 1 and 2A) and modal impact testing method 150 (see FIG. 5) may be used to perform modal impact tests and testing on structures and component parts used in the manufacture and production of air vehicles. Such air vehicles may include commercial aircraft, cargo aircraft, military aircraft, rotorcraft, and other types of aircraft or air vehicles. It may also be appreciated that disclosed embodiments of the modal impact testing assembly 10 (see FIG. 1), the modal impact testing system 12 (see FIG. 2A) and modal impact testing method 150 (see FIG. 5) may be used to perform modal impact tests and testing on structures and component parts used in the manufacture and production of automobiles, trucks, buses, or other suitable transport vehicles.

Figure 2A:
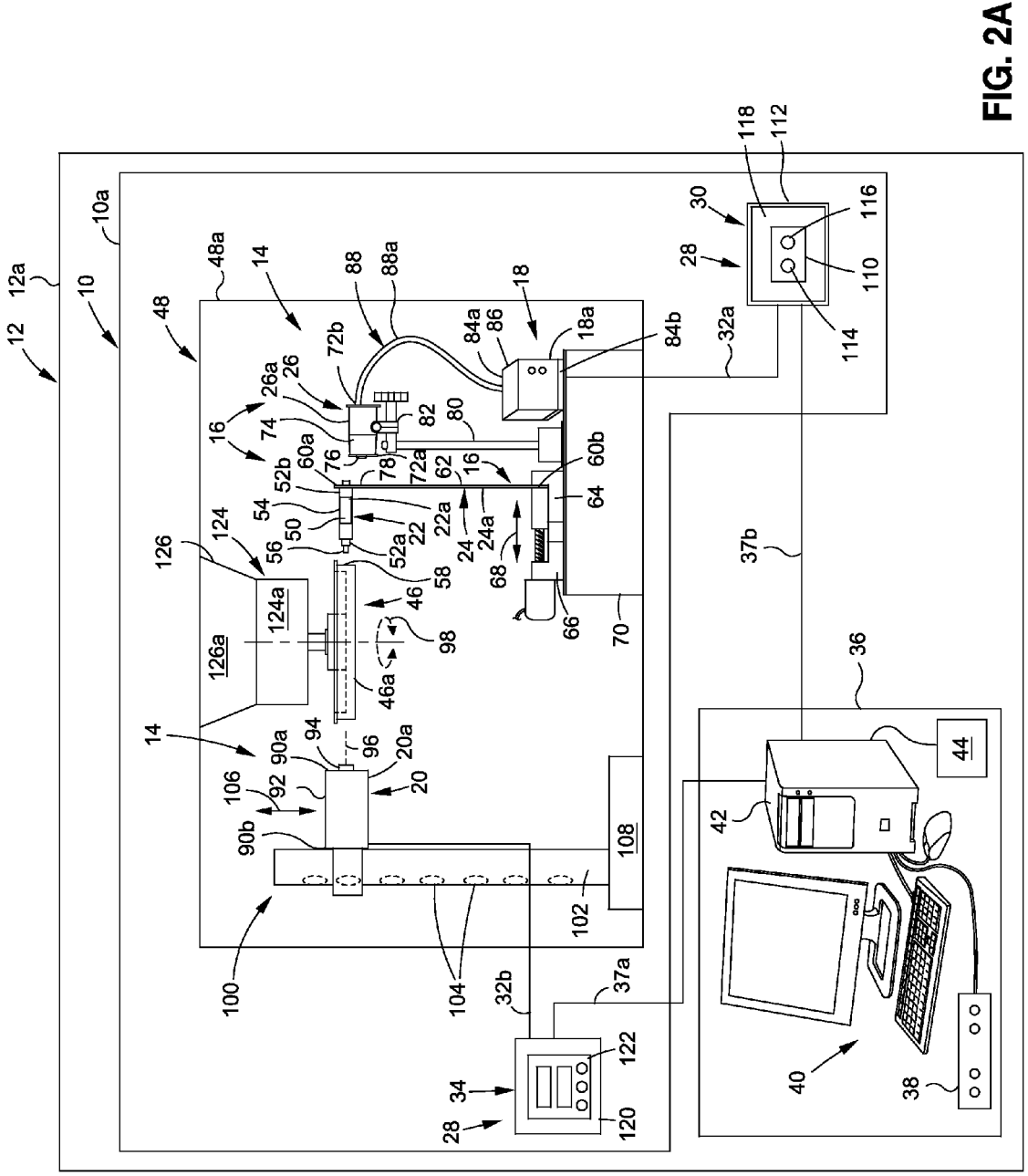
FIG. 2A is an illustration of a perspective view of an embodiment of a modal impact testing assembly and an embodiment of a modal impact testing system of the disclosure.
Figure 4A:
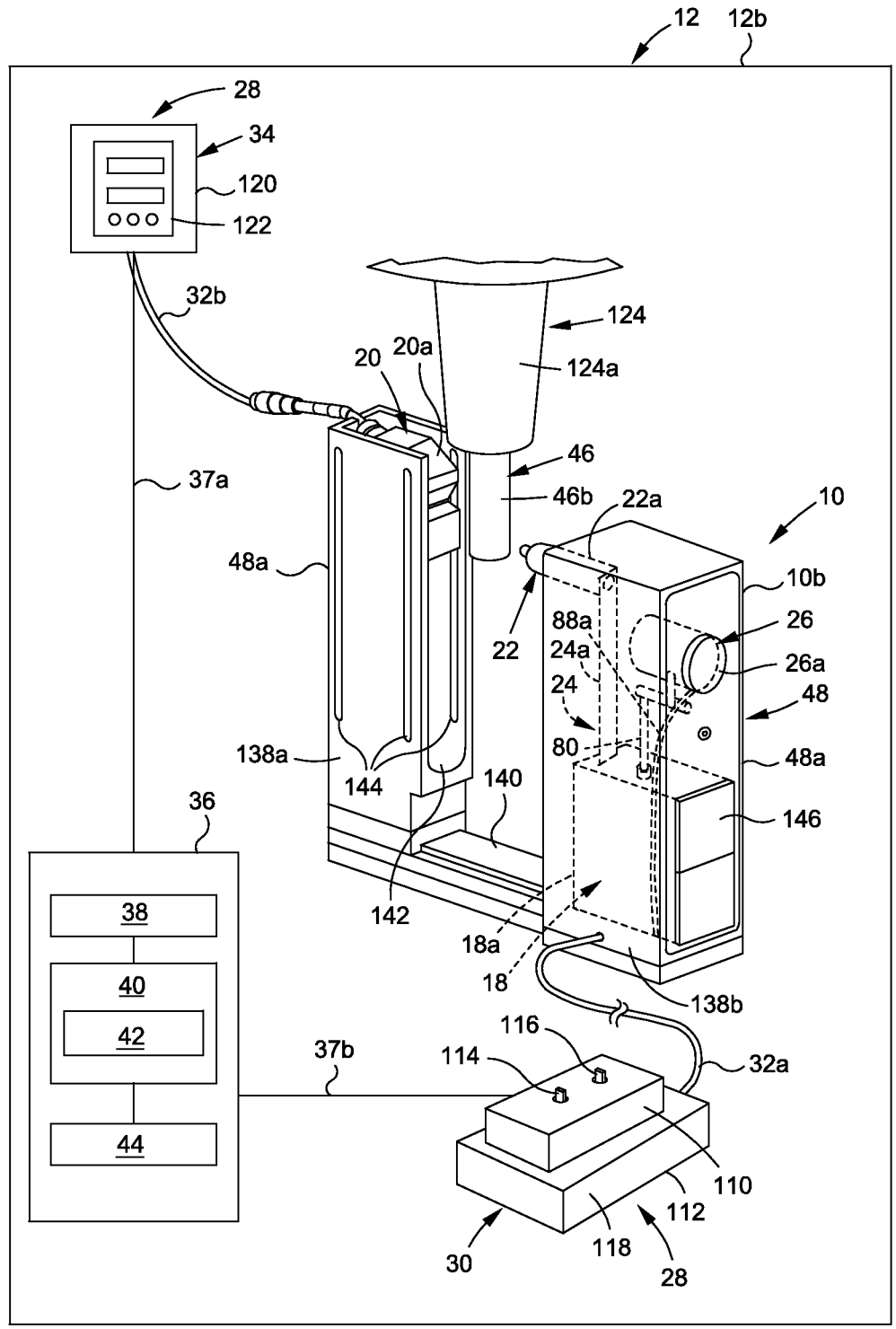
FIG. 4A is an illustration of a side perspective view of another embodiment of a modal impact testing assembly and a modal impact testing system of the disclosure.
Figure 4B:
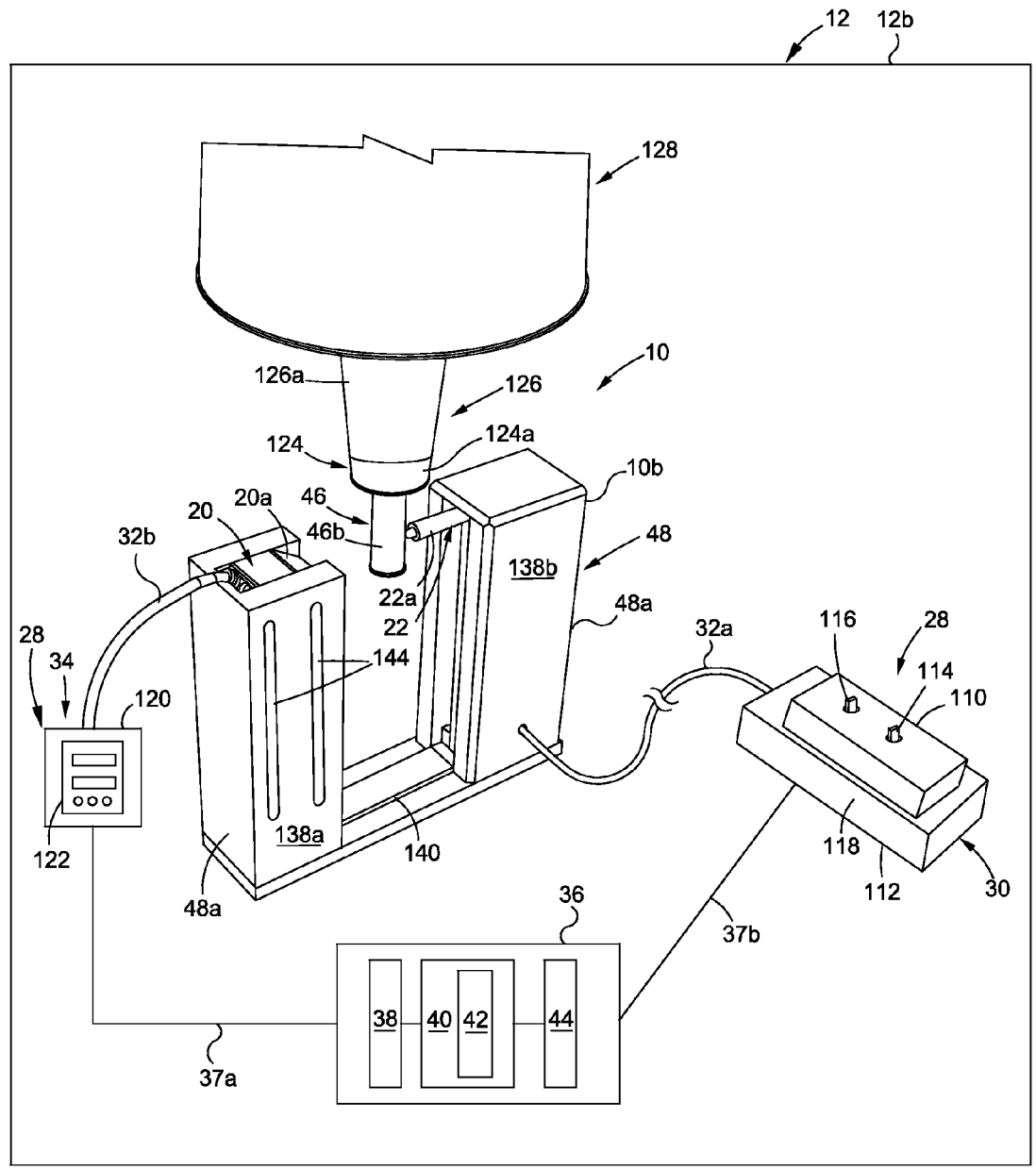
FIG. 4B is an illustration of a top perspective view of the modal impact testing assembly and the modal impact testing system of FIG. 4A.

In one embodiment, there is disclosed a modal impact testing assembly 10 (see FIGS. 1, 2A, 4A). The modal impact testing assembly 10 (see FIGS. 1, 2A, 4A) is preferably part of a modal impact testing system 12 (see FIGS. 1, 2A, 4A). In one embodiment, as shown in FIG. 2A, the modal impact testing assembly 10 may be in the form of a stationary modal impact testing assembly 10a. In another embodiment as shown in FIGS. 4A-4B, the modal impact testing assembly 10 may be in the form of a portable modal impact testing assembly 10b.

As shown in FIG. 1, the modal impact testing assembly 10 comprises a first set of components 14. The first set of components 14 comprise an impact assembly 16, a cycle control element 18 coupled to the impact assembly 16, and a signal response measuring device 20 positioned opposite the impact assembly 16. As further shown in FIG. 1, the impact assembly 16 comprises an impact element 22, an elastically driven element 24, and an actuating element 26.

As shown in FIG. 1, the modal impact testing assembly 10 further comprises a second set of components 28 separate from the first set of components 14. As shown in FIG. 1, the second set of components 28 comprise a first controller 30 coupled to the cycle control element 18 of the first set of components 14. The first controller 30 is preferably configured to control and power the cycle control element 18. The first controller 30 may be coupled to the cycle control element 18 of the first set of components 14 either via a wired connection element 32a (see FIG. 1) or a wireless connection (not shown).

As shown in FIG. 1, the second set of components 28 further comprise a second controller 34 coupled to the signal response measuring device 20 of the first set of components 14. The second controller 34 is preferably configured to control and power the signal response measuring device 20. The second controller 32 may be coupled to the signal response measuring device 20 of the first set of components 14 either via a wired connection element 32b (see FIG. 1) or a wireless connection (not shown).

In another embodiment of the disclosure, there is provided a modal impact testing system 12 (see FIGS. 1, 2A, 4A). In one embodiment as shown in FIG. 2A, the modal impact testing system 12 may be in the form of a stationary modal impact testing system 12a. In another embodiment as shown in FIGS. 4A-4B, the modal impact testing system 12 may be in the form of a portable modal impact testing assembly 12b.

As shown in FIGS. 1 and 2A, the modal impact testing system 12 comprises the modal impact testing assembly 10 and further comprises a data acquisition assembly 36. As shown in FIGS. 1 and 2A, the data acquisition assembly 36 may comprise one or more of a signal analyzer 38, a computer 40, a computer processor 42, a power supply 44, or another suitable data acquisition or data recording device. The power supply 44 preferably comprises an integrated electronics piezoelectric power supply or another suitable power supply.

As shown in FIGS. 1 and 2A, the data acquisition assembly 36 is preferably coupled to the modal impact testing assembly 10 via a first signal cable connection element 37a and via a second signal cable connection element 37b. Alternatively, the data acquisition assembly 36 may be coupled to the modal impact testing assembly 10 via a wireless connection (not shown).

As shown in FIG. 1, the modal impact testing system 12 further comprises a test element 46, discussed in detail below. The modal impact testing assembly 10 and the modal impact testing system 12 enable modal impact testing of the test element 46 while it is rotating at operational speeds.

The first set of components 14 (see FIG. 1) and the second set of components 28 (see FIG. 2) form the modal impact testing assembly 10 (see FIG. 1) for modal impact testing. The impact assembly 16 (see FIG. 1) of the modal impact testing assembly 10 (see FIG. 1) is configured to impact the test element 46 (see FIG. 1) while the test element 46 (see FIG. 1) is rotating at operational speeds. The modal impact testing assembly 10 (see FIG. 1), the test element (see FIG. 1), and the data acquisition assembly 36 (see FIG. 1) together comprise the modal impact testing system 12 (see FIG. 1) for modal impact testing of the test element 46 (see FIG. 1) rotating at operational speeds.

FIG. 2A is an illustration of a perspective view of an embodiment of the modal impact testing assembly 10 and an embodiment of the modal impact testing system 12 of the disclosure. As shown in FIG. 2A, the modal impact testing assembly 10 is in the form of the stationary modal impact testing assembly 10*a*, and the modal impact testing system 12 is in the form of the stationary modal impact testing system 12*a*. As shown in FIG. 2A, the first set of components 14 and the test element 46 are contained within a housing structure 48, such as in the form of a stationary housing structure 48*a*. The housing structure 48 is preferably an enclosure that is not accessible by an operator while the modal impact testing is being performed.

FIG. 2A shows the first set of components 14 comprising the impact assembly 16, the cycle control element 18 coupled to the impact assembly 16, and the signal response measuring device 20 positioned opposite the impact assembly 16. FIG. 2A further shows the impact assembly 16 comprising the impact element 22, the elastically driven element 24, and the actuating element 26. FIG. 2A further shows the second set of components 28 separate from the first set of components 14. The second set of components 28 comprise the first controller 30 (see FIG. 2A) coupled to the cycle control element 18 (see FIG. 2A) via the wired connection element 32*a* (see FIG. 2A). The second set of components 28 further comprise the second controller 34 (see FIG. 2A) coupled to the signal response measuring device 20 (see FIG. 2A) via the wired connection element 32*b* (see FIG. 2A).

With respect to the first set of components 14, as shown in FIG. 2A, the impact element 22 of the impact assembly 16 preferably comprises an impact hammer 22*a*. The impact hammer 22*a* preferably has a load cell 50 (see FIG. 2A) configured to release an impact force output when the impact element 22 impacts the test element 46 (see FIG. 2A). As further shown in FIG. 2A, the impact element 22, such as in the form of impact hammer 22*a*, comprises a first end 52*a*, a second end 52*b*, and a body portion 54. Preferably, the first end 52*a* has a tip portion 56 (see FIG. 2A) configured to impact a portion 58 (see FIG. 2A) of the test element 46 (see FIG. 2A). The impact hammer 22*a* (see FIGS. 2A, 4A) is preferably tuned in a modal manner and preferably emits a remotely-triggered excitation impulse.

As shown in FIG. 2A, the elastically driven element 24 of the impact assembly 16 preferably comprises a tuned-length leaf spring 24*a* and is preferably attached to the impact element 22. As further shown in FIG. 2A, the elastically driven element 24, such as in the form of tuned-length leaf spring 24*a*, comprises a first end 60*a*, a second end 60*b*, and an elongated body portion 62. As further shown in FIG. 2A, the first end 60*a* of the elastically driven element 24, such as in the form of tuned-length leaf spring 24*a*, may be coupled or attached to the second end 52*b* of the impact element 22, such as in the form of impact hammer 22*a*. As further shown in FIG. 2A, the second end 60*b* of the elastically driven element 24, such as in the form of tuned-length leaf spring 24*a*, may be coupled or attached to a base portion 64. The base portion 64 may have an adjustable element 66 (see FIG. 2A) configured to adjust the position of the elastically driven element 24, as well as the impact element 22 attached to the elastically driven element, back and forth in a horizontal direction, as shown by arrow 68 (see FIG. 2A). The base portion 64 may be coupled to a platform element 70 (see FIG. 2A).

As shown in FIG. 2A, the actuating element 26 of the impact assembly 16 preferably comprises an electromagnetic solenoid 26*a*. The electromagnetic solenoid 26*a* is preferably configured to actuate the impact element 22 and the elastically driven element 24, so that the impact element 22 impacts the test element 46. As further shown in FIG. 2A, the actuating element 26, such as in the form of electromagnetic solenoid 26*a*, comprises a first end 72*a*, a second end 72*b*, and a body portion 74. The first end 72*a* of the actuating element 26, such as in the form of electromagnetic solenoid 26*a*, preferably has a magnetic tip portion 76 (see also FIG. 3B). The magnetic tip portion 76 is preferably designed to contact, hold, and release a portion 78 (see also FIG. 3B) of the elongated body portion 62 of the elastically driven element 24, such as in the form of tuned-length leaf spring 24*a*, when the modal impact testing is performed on the test element 46.

As further shown in FIG. 2A, the body portion 74 of the actuating element 26, such as in the form of electromagnetic solenoid 26*a*, is preferably coupled or attached to an upright stand 80 having an attachment portion 82 configured to attach the actuating element 26 to the upright stand 80. The upright stand 80 may be coupled to the platform element 70 (see FIG. 2A).

As shown in FIG. 2A, the cycle control element 18 of the first set of components 14 preferably comprises a trigger circuit device 18*a*. The trigger circuit device 18*a* is preferably configured to trigger the impact assembly 16, and in particular, the impact element 22 of the impact assembly 16, to impact the test element 46. As further shown in FIG. 2A, the cycle control element 18, such as in the form of trigger circuit device 18*a*, comprises a first end 84*a*, a second end 84*b*, and a body portion 86.

As further shown in FIG. 2A, the first end 84*a* of the cycle control element 18, such as in the form of trigger circuit device 18*a*, is preferably connected to the actuating element 26, such as in the form of electromagnetic solenoid 26*a*. The cycle control element 18 (see FIG. 2A) may be connected to the actuating element 26 (see FIG. 2A) via one or more connector elements 88 (see FIG. 2A), such as in the form of one or more wires 88*a* (see FIG. 2A). As further shown in FIG. 2A, the second end 84*b* of the cycle control element 18, such as in the form of trigger circuit device 18*a*, is preferably connected to the first controller 30 via the wired connection element 32*a*. Alternatively, the cycle control element 18, such as in the form of trigger circuit device 18*a*, may be wirelessly connected to the first controller 30.

As shown in FIG. 2A, the signal response measuring device 20 of the first set of components 14 preferably comprises a laser interferometer device 20*a*, such as a laser interferometer head. The laser interferometer device 20*a* is preferably configured to measure a signal response when the impact assembly 16, and in particular, the impact element 22 of the impact assembly 16, impacts the test element 46.

Preferably, the laser interferometer device 20*a* is a noncontact laser interferometer device that serves as the element providing the signal response. As further shown in FIG. 2A, the signal response measuring device 20, such as in the form of laser interferometer device 20*a*, comprises a first end 90*a*, a second end 90*b*, and a body portion 92. As further shown in FIG. 2A, the first end 90*a* of the signal response measuring device 20, such as in the form of laser interferometer device 20*a*, preferably has a signal response measuring portion 94. The signal response measuring portion 94 is preferably designed to emit a laser beam 96 and measure and provide the signal response of the test element 46, when the test element 46 is rotating during the modal impact testing, in a rotational direction such as shown by arrow 98.

As further shown in FIG. 2A, the second end 90*b* of the signal response measuring device 20, such as in the form of laser interferometer device 20a, is preferably coupled or attached to a height adjustable element 100. The height adjustable element 100 is preferably configured to adjust a height of the signal response measuring device 20, such as in the form of laser interferometer device 20a, so that the signal response measuring portion 94 is aligned with the test element 46.

As further shown in FIG. 2A the height adjustable element 100 may comprise an elongated upright portion 102 having openings 104 along a length of the elongated upright portion 102. The openings 104 may be used for adjustment of the height of the signal response measuring device 20, such as in the form of laser interferometer device 20a, up or down in a vertical direction, such as shown by arrow 106. The elongated upright portion 102 (see FIG. 2A) may be coupled or attached to a base portion 108 (see FIG. 2A).

As further shown in FIG. 2A, the second end 90b of the signal response measuring device 20, such as in the form of laser interferometer device 20a, is preferably connected to the second controller 34 via the wired connection element 32b. Alternatively, the signal response measuring device 20, such as in the form of laser interferometer device 20a, may be wirelessly connected to the second controller 34.

The modal impact testing system 12 (see FIGS. 2A, 4A) comprises the modal impact testing assembly 10 (see FIGS. 2A, 4A). The modal impact testing assembly 10, as discussed above, comprises the first set of components 14 (see FIGS. 2A, 4A). The first set of components 14 comprise the impact assembly 16 (see FIGS. 1, 2A), the cycle control element 18 (see FIGS. 2A, 4A) coupled to the impact assembly 16, and the signal response measuring device 20 (see FIGS. 2A, 4A) positioned opposite the impact assembly 16.

The impact assembly 16 (see FIGS. 2A, 4A) comprises the impact element 22 (see FIGS. 2A, 4A) having the load cell 50 (see FIGS. 2A, 4A) configured to release an impact force output when the impact element 22 impacts the test element 46 (see FIGS. 2A, 4A). The impact assembly 16 (see FIGS. 2A, 4A) further comprises the elastically driven element 24 (see FIGS. 2A, 4A) attached to the impact element 22.

The impact assembly 16 further comprises the actuating element 26 (see FIGS. 2A, 4A). The actuating element 26 (see FIGS. 2A, 4A) is preferably configured to actuate the impact element 22 and the elastically driven element 24 (see FIGS. 2A, 4A), so that the impact element 22 impacts the test element 46. The signal response measuring device 20 preferably comprises the laser interferometer device 20a (see FIGS. 2A, 4A). The laser interferometer device 20a (see FIGS. 2A, 4A) is preferably configured to measure a signal response when the impact assembly 16 impacts the test element 46.

In one embodiment, the modal impact testing system 12 is in the form of the stationary modal impact testing system 12a (see FIG. 2A), and the first set of components 14 (see FIG. 2A) and the test element 46 (see FIG. 2A) are contained within a housing structure 48 (see FIG. 2A), such as a stationary housing structure 48a (see FIG. 2A). In another embodiment, the modal impact testing system 12 is in the form of the portable modal impact testing system 12b (see FIG. 4A), and the first set of components 14 (see FIG. 1) are substantially contained within a housing structure 48 (see FIG. 4B), such as in the form of portable housing structure 48b (see FIG. 4B).

The modal impact testing system 12 (see FIGS. 2A, 4A) further comprises the second set of components 28 (see FIGS. 2A, 4A) separate from the first set of components 14. The second set of components 28 comprise the first controller 30 (see FIGS. 2A, 4A) coupled to the cycle control element 18 of the modal impact testing assembly 10 (see FIGS. 2A, 4A).

With respect to the second set of components 28, as shown in FIG. 2A, the first controller 30 preferably comprises an arm trigger switch 110 and a power element 112. Preferably, the arm trigger switch 110 comprises an arm switch 114 and a trigger switch 116. Preferably, the power element 112 comprises a battery pack 118 (see FIG. 2A) or another suitable source of power. The first controller 30 (see FIG. 2A) is preferably configured to control and power the cycle control element 18 (see FIG. 2A), such as in the form of trigger circuit device 18a (see FIG. 2A). The first controller 30 is preferably coupled to the cycle control element 18, such as in the form of trigger circuit device 18a, via the wired connection element 32a, or via a wireless connection (not shown).

As shown in FIG. 2A, the second controller 34 of the second set of components 28, preferably comprises a laser interferometer controller 120 having a control interface portion 122. The second controller 34 is preferably configured to control and power the signal response measuring device 20, such as in the form of laser interferometer device 20a. The second controller 34 drives a continuous operation of the laser interferometer device 20a. The response signal or output signal from the laser interferometer device 20a is preferably continuous and may be sampled by the data acquisition system 36 as needed. The second controller 34 (see FIG. 2A) is preferably coupled to the signal response measuring device 20 (see FIG. 2A), such as in the form of laser interferometer device 20a (see FIG. 2A), either via the wired connection element 32b (see FIG. 2A), or via a wireless connection (not shown).

As shown in FIG. 2A, the modal impact testing system 12 (see also FIG. 4A) further comprises the data acquisition assembly 36 (see also FIG. 4A). The data acquisition assembly 36 preferably comprises one or more of a signal analyzer 38 (see FIGS. 2A, 4A), a computer 40 (see FIGS. 2A, 4A), a computer processor 42 (see FIGS. 2A, 4A), and a power supply 44 (see FIGS. 2A, 4A). Preferably, the power supply 44 comprises an integrated electronics piezoelectric power supply or another suitable power supply.

The data acquisition assembly 36 (see FIGS. 2A, 4A) may be coupled to the modal impact testing assembly 10 (see FIGS. 2A, 4A) via a first signal cable connection element 37a (see FIGS. 2A, 4A) and via a second signal cable connection element 37b (see FIGS. 2A, 4A). Alternatively, the data acquisition assembly 36 (see FIGS. 2A, 4A) may be coupled to the modal impact testing assembly 10 (see FIGS. 2A, 4A) via a wireless connection (not shown).

Figure 2B:
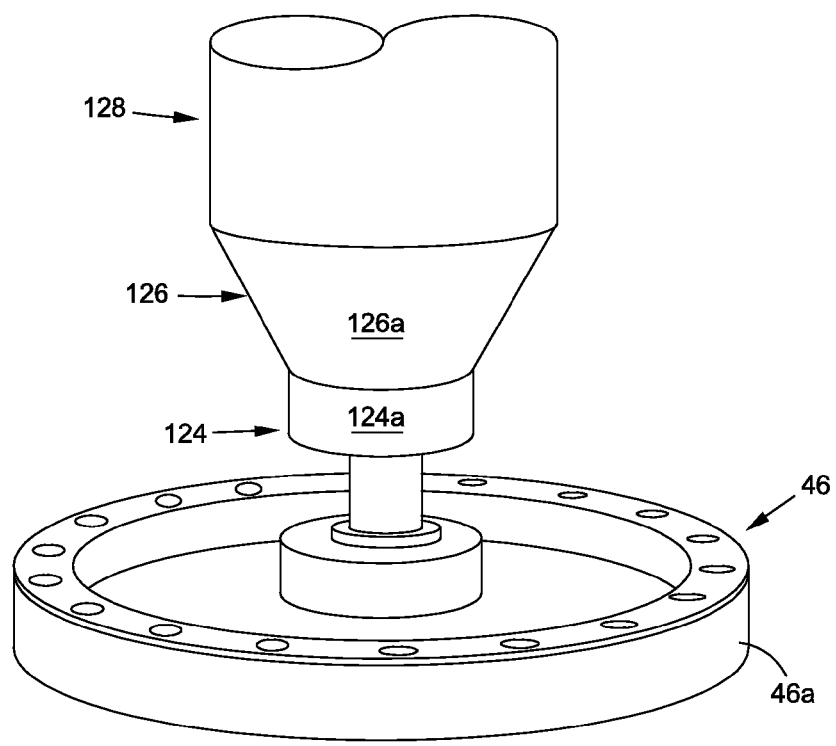
FIG. 2B is an illustration of a close-up perspective view of an embodiment of a test element that may be used in a modal impact testing assembly and a modal impact testing system of the disclosure.

As shown in FIG. 2A, the modal impact testing system 12, such as in the form of stationary modal impact testing system 12a, further comprises the test element 46. In one embodiment as shown in FIGS. 2A-2B, the test element 46 may be in the form of a test disc 46a. FIG. 2B is an illustration of a close-up perspective view of an embodiment of the test element 46, such as in the form of test disc 46a, that may be used in the modal impact testing assembly 10 and the modal impact testing system 12 of the disclosure.

Figure 2C:
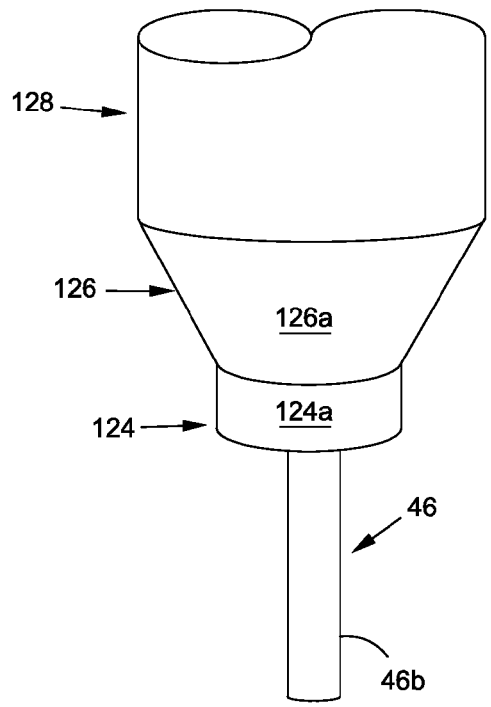
FIG. 2C is an illustration of a close-up perspective view of another embodiment of a test element that may be used in a modal impact testing assembly and a modal impact testing system of the disclosure.

In another embodiment as shown in FIG. 2C, the test element 46 may be in the form of a test bar 46b. FIG. 2C is an illustration of a close-up perspective view of another embodiment of the test element 46, such as in the form of test bar 46b, that may be used in the modal impact testing assembly 10 and the modal impact testing system 12 of the disclosure. Alternatively, the test element 46 may be of another suitable form or configuration.

As shown in FIG. 2A, the test element 46 is preferably configured for placement between and alignment with the impact assembly 16 and the signal response measuring device 20. As shown in FIGS. 2A-2C, the test element 46 is preferably secured to a holding element 124, such as in the form of a tool holder 124a. The holding element 124, such as in the form of tool holder 124a, is preferably attached to a rotating element 126, such as in the form of a spindle 126a. The rotating element 126, such as in the form of spindle 126a, is preferably part of a machining apparatus 128 (see FIGS. 2B-2C).

The machining apparatus 128 (see FIGS. 2B-2C) may comprise a machining tool machine, a rotating cutting machine, a CNC (computer numerical control) machine, or another suitable machining apparatus that may undergo modal impact testing. In particular, any machining apparatus with a rotating element may be tested. In addition, any element of any machining apparatus where modal information may be required from a non-manually applied impact hammer test may be tested.

Preferably, the test element 46 has a substantially similar mass to a mass of an existing or known cutting device of an existing or known machining apparatus or tool machine, such as a rotating cutting machine or CNC (computer numerical control) machine. The modal impact testing assembly 10 and the modal impact testing system 12 enable modal impact testing of the test element 46 while it is rotating at operational speeds.

Figure 3A:
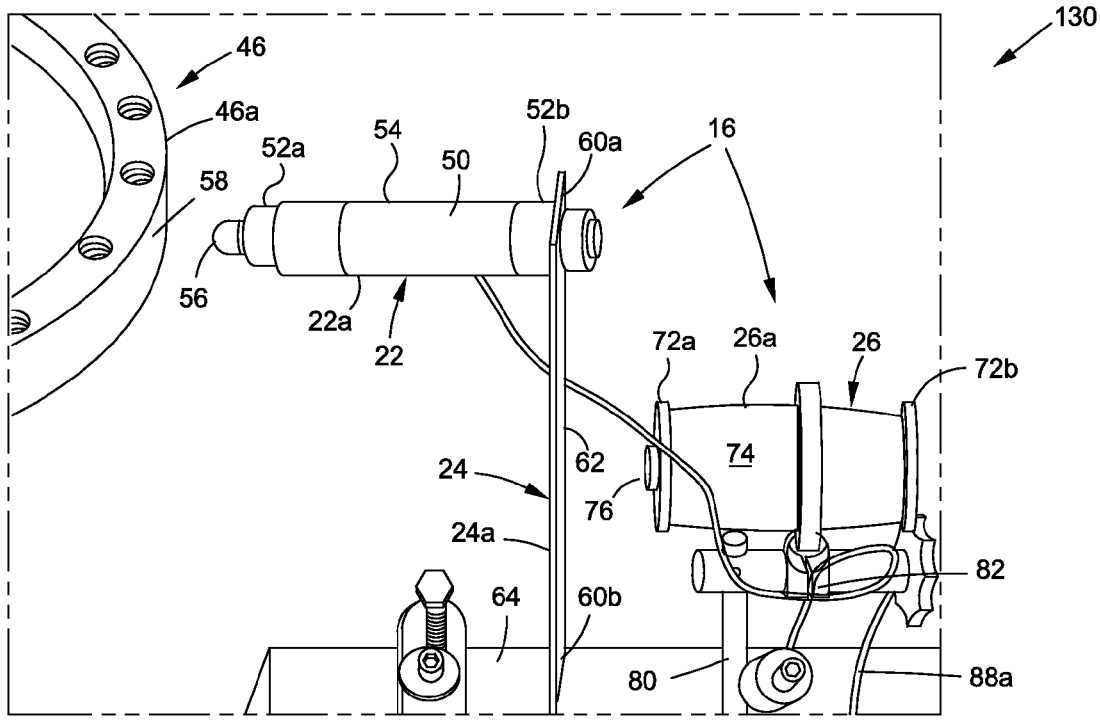
FIG. 3A is an illustration of a close-up perspective side view of an embodiment of an impact assembly shown in a first position in relation to an embodiment of a test element that may be used in a modal impact testing assembly and a modal impact testing system of the disclosure.

FIGS. 3A-3D show the various positions of the impact element 22 of the impact assembly 16 in relation to the test element 46 during an impact test cycle. FIG. 3A is an illustration of a close-up perspective side view of an embodiment of the impact assembly 16 shown in a first position 130 in relation to an embodiment of the test element 46, such as in the form of test disc 46a, that may be used in the modal impact testing assembly 10 (see FIGS. 2A, 4A) and the modal impact testing system 12 (see FIGS. 2A, 4A) of the disclosure.

FIG. 3A also depicts that in the first position 130, the impact assembly 16 is not armed and not in operation. FIG. 3A shows the impact element 22, such as in the form of impact hammer 22a, having the first end 52a with the tip portion 56, the second end 52b, and the body portion 54 with the load cell 50. The tip portion 56 (see FIG. 3A) is preferably configured to impact a portion 58 (see FIG. 3A) of the test element 46 (see FIG. 3A), such as in the form of test disc 46a.

As shown in FIG. 3A, the second end 52b of the impact element 22, such as in the form of impact hammer 22a, is preferably attached or coupled to the first end 60a of the elastically driven element 24, such as in the form of tuned-length leaf spring 24a. As further shown in FIG. 3A, the second end 60b of the elastically driven element 24, such as in the form of tuned-length leaf spring 24a, may be coupled or attached to the base portion 64.

As further shown in FIG. 3A, the first end 72a of the actuating element 26, such as in the form of electromagnetic solenoid 26a, preferably has the magnetic tip portion 76. The magnetic tip portion 76 is preferably designed to contact, hold, and release the portion 78 (see FIG. 3B) of the elongated body portion 62 (see FIG. 3A) of the elastically driven element 24 (see FIG. 3A), such as in the form of tuned-length leaf spring 24a (see FIG. 3A), when the modal impact testing is performed on the test element 46 (see FIG. 3A). As further shown in FIG. 3A, the body portion 74 of the actuating element 26, such as in the form of electromagnetic solenoid 26a, is preferably coupled or attached to the upright stand 80. The upright stand 80 (see FIG. 3A) preferably has the attachment portion 82 (see FIG. 3A) configured to attach the actuating element 26 (see FIG. 3A) to the upright stand 80 (see FIG. 3A).

As further shown in FIG. 3A, the actuating element 26, such as in the form of electromagnetic solenoid 26a, may be coupled or attached to the cycle control element 18 (see FIG. 2A) via one or more wires 88a. As shown in FIG. 3A, in the first position 130, the impact element 22 is not in contact with the test element 46, and the elastically driven element 24 is not in contact with the actuating element 26.

Figure 3B:
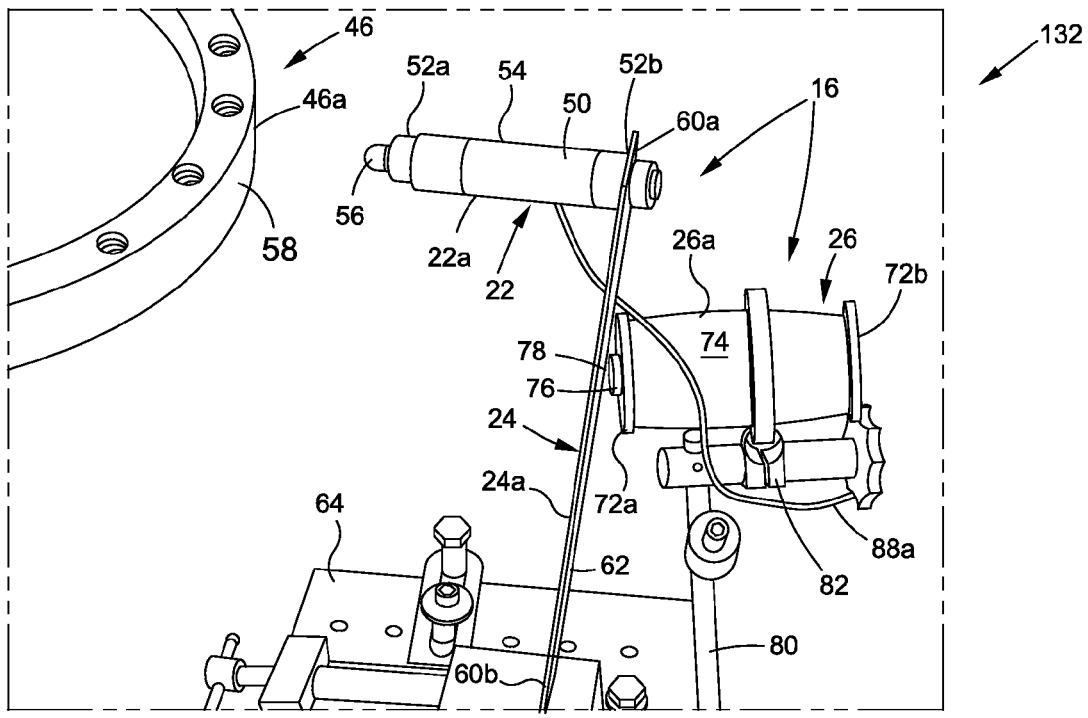
FIG. 3B is an illustration of a close-up perspective side view of the impact assembly of FIG. 3A shown in a second position in relation to the test element of FIG. 3A.

FIG. 3B is an illustration of a close-up perspective side view of the impact assembly 16 of FIG. 3A shown in a second position 132 in relation to the test element 46, such as in the form of test disc 46a, of FIG. 3A. In the second position 132, the arm switch 114 (see FIGS. 2A, 4A) of the arm trigger switch 110 (see FIGS. 2A, 4A) is turned on or activated. This causes the impact element 22 and the elastically driven element 24 to be moved backwards, so that the portion 78 of the elastically driven element 24, which is preferably made of a metal material, contacts the magnetic tip portion 76 of the actuator element 26. The magnetic tip portion 76 of the actuator element 26 holds the portion 78 of the elastically driven element 24 in the second position 132, which is an armed position.

FIG. 3B shows the impact element 22, such as in the form of impact hammer 22a, having the first end 52a with the tip portion 56, the second end 52b, and the body portion 54 with the load cell 50. The tip portion 56 (see FIG. 3B) is preferably configured to impact portion 58 (see FIG. 3B) of the test element 46 (see FIG. 3B), such as in the form of test disc 46a. As shown in FIG. 3B, the second end 52b of the impact element 22, such as in the form of impact hammer 22a, is preferably attached or coupled to the first end 60a of the elastically driven element 24, such as in the form of tuned-length leaf spring 24a. The second end 60b (see FIG. 3B) of the elastically driven element 24 (see FIG. 3B), such as in the form of tuned-length leaf spring 24a (see FIG. 3B), may be coupled or attached to the base portion 64 (see FIG. 3B).

As further shown in FIG. 3B, the first end 72a of the actuating element 26, such as in the form of electromagnetic solenoid 26a, preferably has the magnetic tip portion 76. The magnetic tip portion 76 is preferably designed to contact, hold, and release the portion 78 of the elongated body portion 62 of the elastically driven element 24, such as in the form of tuned-length leaf spring 24a, when the modal impact testing is performed on the test element 46. As further shown in FIG. 3B, the body portion 74 of the actuating element 26, such as in the form of electromagnetic solenoid 26a, is preferably coupled or attached to the upright stand 80 having the attachment portion 82.

With continued reference to FIG. 3B, the actuating element 26, such as in the form of electromagnetic solenoid 26a, may be coupled or attached to the cycle control element 18 (see FIG. 2A) via one or more wires 88a. As shown in FIG. 3B, in the second position 132, the impact element 22 is not in contact with the test element 46, but the elastically driven element 24 is now in contact with the actuating element 26, and the actuating element 26 holds the elastically driven element 24. The actuating element 26, such as in the form of electromagnetic solenoid 26a, creates a magnetic field that draws the elastically driven element 24, such as in the form of tuned-length leaf spring 24a, back and holds it until the charge is interrupted and then releases it.

Figure 3C:
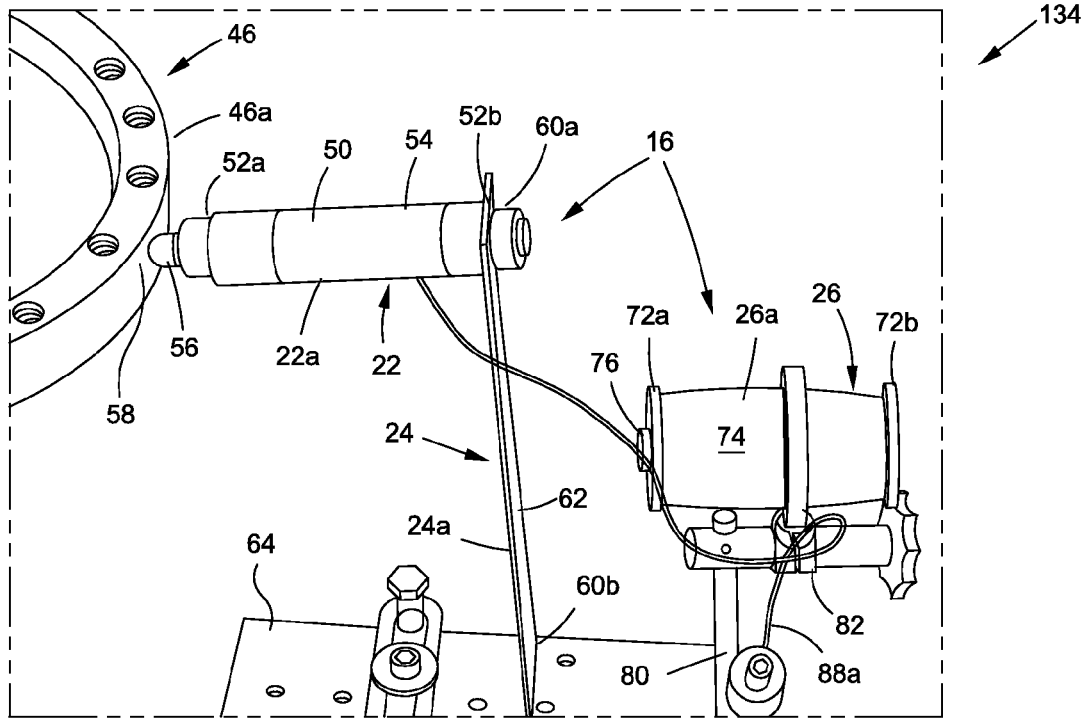
FIG. 3C is an illustration of a close-up perspective side view of the impact assembly of FIG. 3A shown in a third position in relation to the test element of FIG. 3A.

FIG. 3C is an illustration of a close-up perspective side view of the impact assembly 16 of FIG. 3A shown in a third position 134 in relation to the test element 46, such as in the form of test disc 46a, of FIG. 3A. In the third position 134, or triggered position, the trigger switch 116 (see FIGS. 2A, 4A) of the arm trigger switch 110 (see FIGS. 2A, 4A) is turned on or activated. This causes the actuating element 26, such as in the form of electromagnetic solenoid 26a, to release the elongated body portion 62 of the elastically driven element 24, such as in the form of tuned-length leaf spring 24a. Upon release of the elastically driven element 24 (see FIG. 3C), the impact element 22, such as in the form of impact hammer 22a, and the elastically driven element 24, such as in the form of tuned-length leaf spring 24a, spring forward with a spring force toward the test element 46. This causes the tip portion 56 of the impact element 22 to impact or contact the portion 58 of the test element 46.

FIG. 3C shows the impact element 22, such as in the form of impact hammer 22a, having the first end 52a with the tip portion 56, the second end 52b, and the body portion 54 with the load cell 50. As shown in FIG. 3C, the second end 52b of the impact element 22, such as in the form of impact hammer 22a, is preferably attached or coupled to the first end 60a of the elastically driven element 24, such as in the form of tuned-length leaf spring 24a. The second end 60b (see FIG. 3C) of the elastically driven element 24 (see FIG. 3C), such as in the form of tuned-length leaf spring 24a (see FIG. 3C), may be coupled or attached to the base portion 64 (see FIG. 3C).

As further shown in FIG. 3C, the first end 72a of the actuating element 26, such as in the form of electromagnetic solenoid 26a, preferably has the magnetic tip portion 76 that is designed to contact, hold, and release the portion 78 (see FIG. 3B) of the elongated body portion 62 of the elastically driven element 24, such as in the form of tuned-length leaf spring 24a, when the modal impact testing is performed on the test element 46. As further shown in FIG. 3C, the body portion 74 of the actuating element 26, such as in the form of electromagnetic solenoid 26a, is preferably coupled or attached to the upright stand 80 having the attachment portion 82.

As further shown in FIG. 3C, the actuating element 26, such as in the form of electromagnetic solenoid 26a, may be coupled or attached to the cycle control element 18 (see FIG. 2A) via one or more wires 88a. As shown in FIG. 3C, in the third position 134, the impact element 22 is in contact with the test element 46, but the elastically driven element 24 is not in contact with the magnetic tip portion 76 of the actuating element 26.

Figure 3D:
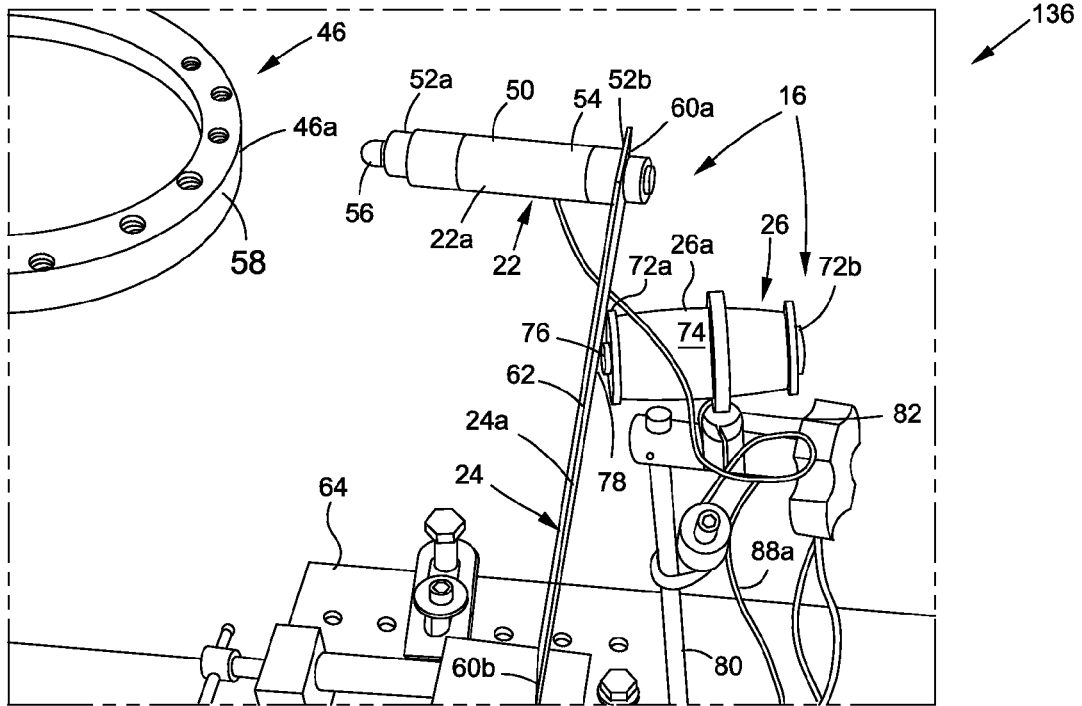
FIG. 3D is an illustration of a close-up perspective side view of the impact assembly of FIG. 3A shown in a fourth position in relation to the test element of FIG. 3A.

FIG. 3D is an illustration of a close-up perspective side view of the impact assembly 16 of FIG. 3A shown in a fourth position 136 in relation to the test element 46, such as in the form of test disc 46a, of FIG. 3A. In the fourth position 136, after the impact element 22, such as in the form of impact hammer 22a, has impacted the test element 46, the actuating element 26, such as in the form of electromagnetic solenoid 26a, is reenergized and recaptures the elastically driven element 24, such as in the form of tuned-length leaf spring 24a. This causes the impact element 22 (see FIG. 3D) and the elastically driven element 24 (see FIG. 3D), such as in the form of tuned-length leaf spring 24a (see FIG. 3D), to spring back on the rebound from the impact of portion 58 (see FIG. 3D) of the test element 46 (see FIG. 3D).

With continued reference to FIG. 3D, the magnetic tip portion 76 of the first end 72a of the actuator element 26 holds the portion 78 of the elongated body portion 62 of the elastically driven element 24 in the fourth position 136. The fourth position 136 is a post-trigger position. FIG. 3D shows the impact element 22, such as in the form of impact hammer 22a, having the first end 52a with the tip portion 56, the second end 52b, and the body portion 54 with the load cell 50. As shown in FIG. 3D, the second end 52b of the impact element 22 is preferably attached or coupled to the first end 60a of the elastically driven element 24. As further shown in FIG. 3D, the second end 60b of the elastically driven element 24 may be coupled or attached to the base portion 64.

As further shown in FIG. 3D, the body portion 74 of the actuating element 26, such as in the form of electromagnetic solenoid 26a, is preferably coupled or attached to the upright stand 80. Attachment portion 82 (see FIG. 3D) is preferably configured to attach the actuating element 26 to the upright stand 80.

As further shown in FIG. 3D, the actuating element 26, such as in the form of electromagnetic solenoid 26a, may be coupled or attached to the cycle control element 18 (see FIG. 2A) via one or more wires 88a. As shown in FIG. 3D, in the fourth position 136, the impact element 22 is not in contact with the test element 46, and the elastically driven element 24 is in contact with the actuating element 26. The actuating element 26 holds the elastically driven element 24.

FIGS. 4A-4B show another embodiment of the modal impact testing assembly 10, such as in the form of portable modal impact testing assembly 10b. FIGS. 4A-4B further show another embodiment of the modal impact testing system 12, such as in the form of portable modal impact testing system 12b.

FIG. 4A is an illustration of a side perspective view of the modal impact testing assembly 10, such as in the form of portable modal impact testing assembly 10b. In addition, FIG. 4A is an illustration of a side perspective view of the modal impact testing system 12, such as in the form of portable modal impact testing system 12b, of the disclosure.

FIG. 4B is an illustration of a top perspective view of the modal impact testing assembly 10, such as in the form of portable modal impact testing assembly 10b. In addition, FIG. 4B is an illustration of a top perspective view of the modal impact testing system 12, such as in the form of portable modal impact testing system 12b, of FIG. 4A.

As shown in FIGS. 4A-4B, the modal impact testing assembly 10, such as in the form of portable modal impact testing assembly 10b, includes a housing structure 48, such as in the form of a portable housing structure 48b. As shown in FIGS. 4A-4B, the housing structure 48, such as in the form of portable housing structure 48b, comprises a first tower portion 138a, a second tower portion 138b, and a base portion 140. The base portion 140 (see FIGS. 4A-4B) is preferably positioned between the base of the first tower portion 138a and the base of the second tower portion 138b.

As shown in FIGS. 4A-4B, the first tower portion 138a houses the signal response measuring device 20, such as in the form of laser interferometer device 20a. As further shown in FIG. 4A, the first tower portion 138a may have an elongated cut-out portion 142 and a plurality of elongated slots 144 (see also FIG. 4B). The elongated slots 144 are preferably configured to allow the signal response measuring device 20, such as in the form of laser interferometer device 20a, to slide vertically up and down within the first tower portion 138a, as necessary. This, in turn, allows alignment of the signal response measuring device 20 (see FIG. 4A) with the test element 46 (see FIG. 4A), such as in the form of test bar 46b (see FIG. 4A).

As shown in FIGS. 4A-4B, the second tower portion 138b houses the impact element 22, such as in the form of impact hammer 22a. As further shown in FIG. 4A, the second tower portion 138b houses the elastically driven element 24, such as in the form of tuned-length leaf spring 24a. The second tower portion 138b (see FIG. 4A) further houses the actuating element 26 (see FIG. 4A), such as in the form of electromagnetic solenoid 26a, which is attached to upright stand 80 (see FIG. 4A).

The second tower portion 138b (see FIG. 4A) further houses the cycle control element 18 (see FIG. 4A), such as in the form of trigger circuit device 18a. The cycle control element 18 (see FIG. 4A) is preferably connected to the actuating element 26 (see FIG. 4A) via one or more wires 88*a* (see FIG. 4A). As further shown in FIG. 4A, the second tower portion 138*b* comprises access portion 146 to allow access to the impact element 22, the elastically driven element 24, the actuating element 26, and the cycle control element 18.

As shown in FIGS. 4A-4B, the test element 46, such as in the form of test bar 46*b*, is positioned between the first tower portion 138*a* and the second tower portion 38*b*. As further shown in FIGS. 4A-4B, the test element 46 is preferably coupled or attached to holding element 124, such as in the form of tool holder 124*a*. As shown in FIG. 4B, the holding element 124 is preferably attached to the rotating element 126, such as a spindle 126*a*. The rotating element 126 (see FIG. 4B) is preferably attached to a machining apparatus 128 (see FIG. 4B).

The distance between the first tower portion 138*a* (see FIG. 4A) and the second tower portion 138*b* (see FIG. 4A) is preferably adjustable at the base portion 140 (see FIG. 4A). This allows varying strength of impact of the impact element 22, such as the impact hammer 22*a*, against the test element 46.

As shown in FIGS. 4A-4B, the modal impact testing assembly 10, such as in the form of portable modal impact testing assembly 10*b*, may further comprise a second set of components 28. The second set of components 28 comprises the first controller 30 coupled to the cycle control element 18 via the wired connection element 32*a* or via a wireless connection (not shown). The second set of components 28 further comprises the second controller 34 coupled to the signal response measuring device 20 via the wired connection element 32*b* or via a wireless connection (not shown).

As shown in FIGS. 4A-4B, the first controller 30 preferably comprises the arm trigger switch 110 and the power element 112. Preferably, the arm trigger switch 110 comprises the arm switch 114 (see FIGS. 4A-4B) and the trigger switch 116 (see FIGS. 4A-4B). Preferably, the power element 112 comprises the battery pack 118 (see FIGS. 4A-4B) or another suitable source of power. The first controller 30 (see FIGS. 4A-4B) is preferably configured to control and power the cycle control element 18 (see FIG. 4A), such as in the form of trigger circuit device 18*a* (see FIG. 4A).

As shown in FIGS. 4A-4B, the second controller 34 preferably comprises a laser interferometer controller 120 having a control interface portion 122. The second controller 34 is preferably configured to control and power the signal response measuring device 20 (see FIGS. 4A-4B), such as in the form of laser interferometer device 20*a* (see FIGS. 4A-4B).

As shown in FIGS. 4A-4B, the modal impact testing system 12, such as in the form of portable modal impact testing system 12*b*, further comprises a data acquisition assembly 36. As shown in FIGS. 4A-4B, the data acquisition assembly 36 comprises one or more of a signal analyzer 38, a computer 40, a computer processor 42, and a power supply 44. The power supply 44 preferably comprises an integrated electronics piezoelectric power supply or another suitable power supply. As shown in FIGS. 4A-4B, the data acquisition assembly 36 is preferably coupled to the first controller 30 and the second controller 34 of the modal impact testing assembly 10, such as in the form of portable modal impact testing assembly 10*b*.

As further shown in FIGS. 4A-4B, the data acquisition assembly 36 is preferably coupled to the second controller 34 via a first signal cable connection element 37*a*. As further shown in FIGS. 4A-4B, the data acquisition assembly 36 is preferably coupled to the first controller 30 via a second signal cable connection element 37*b*. Alternatively, the data acquisition assembly 36 may be coupled to the first controller 30 and to the second controller 34 via a wireless connection (not shown).

Figure 5:
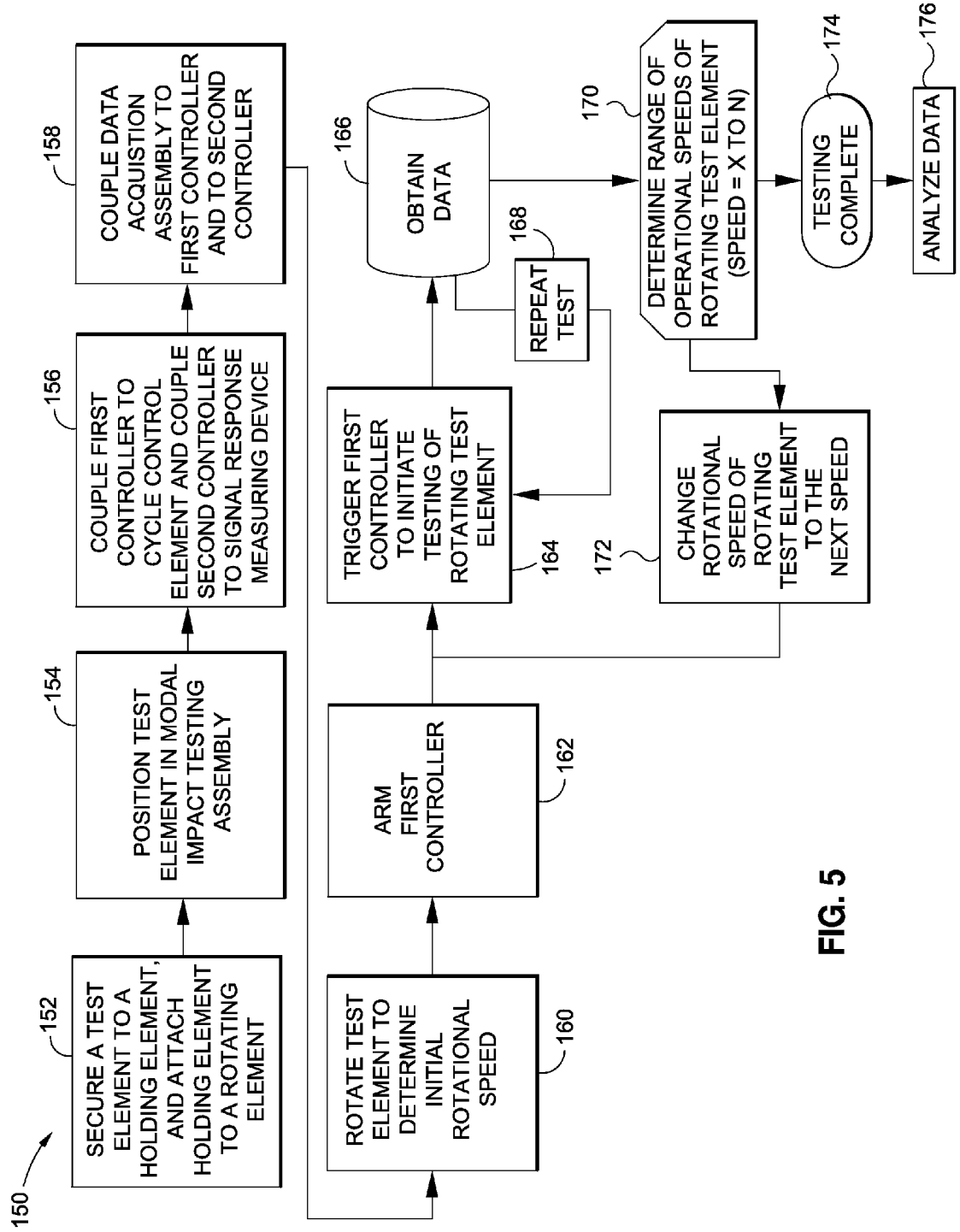
FIG. 5 is an illustration of a schematic diagram of an embodiment of a modal impact testing method of the disclosure.

In another embodiment of the disclosure, there is provided a modal impact testing method 150 (see FIG. 5). FIG. 5 is an illustration of a schematic diagram of an embodiment of the modal impact testing method 150 of the disclosure. As shown in FIG. 5, the method 150 comprises step 152 of securing a test element 46 (see FIGS. 2A-2C) to a holding element 124 (see FIGS. 2A-2C). Step 152 further comprises attaching the holding element 124 to a rotating element 126 (see FIGS. 2A-2C) of a machining apparatus 128 (see FIGS. 2B-2C).

As shown in FIG. 5, the method 150 further comprises step 154 of positioning the test element 46 (see FIGS. 2A, 4A) in relation to a modal impact testing assembly 10 (see FIGS. 2A, 4A) by aligning the test element 46 between an impact assembly 16 (see FIGS. 2A, 4A) and a signal response measuring device 20 (see FIGS. 2A, 4A) of the modal impact testing assembly 10. The aligning of the test element 46 (see FIGS. 2A, 4A) between the impact assembly 16 (see FIGS. 2A, 4A) and the signal response measuring device 20 (see FIGS. 2A, 4A) preferably comprises aligning the test element 46 (see FIGS. 2A, 4A) between an impact element 22 (see FIGS. 2A, 4A), such as in the form of impact hammer 22*a* (see FIGS. 2A, 4A). The impact hammer 22*a* (see FIGS. 2A, 4A) is preferably configured to impact the test element 46 (see FIGS. 2A, 4A).

The signal response measuring device 20 (see FIGS. 2A, 4A), such as in the form of laser interferometer device 20*a* (see FIGS. 2A, 4A), is preferably configured to measure a response signal from the test element 46 (see FIGS. 2A, 4A) after impact with the impact element 22 (see FIGS. 2A, 4A), such as in the form of impact hammer 22*a*. The step 154 of positioning the test element 46 in relation to the modal impact testing assembly 10 may further comprise positioning the test element 46 in relation to either a stationary modal impact testing assembly 10*a* (see FIG. 2A), or to a portable modal impact testing assembly 10*b* (see FIG. 4A).

As shown in FIG. 5, the method 150 further comprises step 156 of coupling a first controller 30 (see FIGS. 2A, 4A) to a cycle control element 18 (see FIGS. 2A, 4A) of the modal impact testing assembly 10 (see FIGS. 2A, 4A). Step 156 further comprises coupling a second controller 34 (see FIGS. 2A, 4A) to the signal response measuring device 20 (see FIGS. 2A, 4A) of the modal impact testing assembly 10 (see FIGS. 2A, 4A).

As discussed in detail above, the first controller 30 (see FIGS. 2A, 4A) preferably comprises the arm trigger switch 110 (see FIGS. 2A, 4A) and the power element 112 (see FIGS. 2A, 4A). Preferably, the arm trigger switch 110 (see FIGS. 2A, 4A) comprises the arm switch 114 (see FIGS. 2A, 4A) and the trigger switch 116 (see FIGS. 2A, 4A). Preferably, the power element 112 (see FIGS. 2A, 4A) comprises the battery pack 118 (see FIGS. 2A, 4A) or another suitable source of power. As discussed in detail above, the second controller 34 (see FIGS. 2A, 4A) preferably comprises a laser interferometer controller 120 (see FIGS. 2A, 4A) having a control interface portion 122 (see FIGS. 2A, 4A).

As shown in FIG. 5, the method 150 further comprises step 158 of coupling a data acquisition assembly 36 (see FIGS. 2A, 4A) to the first controller 30 (see FIGS. 2A, 4A) and to the second controller 34 (see FIGS. 2A, 4A). The step 158 of coupling the data acquisition assembly 36 to the first controller 30 and to the second controller 34 further comprises coupling a data acquisition assembly 36 comprising one or more of a signal analyzer 38 (see FIGS. 2A, 4A), a computer 40 (see FIGS. 2A, 4A), a computer processor 42 (see FIGS. 2A, 4A), and a power supply 44 (see FIGS. 2A, 4A). Preferably, the power supply 44 comprises an integrated electronics piezoelectric power supply or another suitable power supply.

The data acquisition assembly 36 (see FIGS. 2A, 4A) is preferably coupled to the first controller 30 (see FIGS. 2A, 4A) via the second signal cable connection element 37b (see FIGS. 2A, 4A). The data acquisition assembly 36 (see FIGS. 2A, 4A) is preferably coupled to the second controller 34 (see FIGS. 2A, 4A) via the first signal cable connection elements 37a (see FIGS. 2A, 4A). Alternatively, the data acquisition assembly 36 may be coupled to the first controller 30 and to the second controller 34 via a wireless connection (not shown).

As shown in FIG. 5, the method 150 further comprises step 160 of rotating the test element 46 (see FIGS. 2A, 4A) to determine an initial rotational speed. Some rotational speeds may not work as well as other rotational speeds due to vibrational characteristics of the rotating element 126 (see FIGS. 2B, 4B) or machining apparatus 128 (see FIGS. 2B, 4B). It is preferable to avoid chatter (regenerative vibration) by a known cutting device. Such chatter may result from the interplay of resonant frequency with input forces and vibration, as the known cutting device moves through a material being machined.

As shown in FIG. 5, the method 150 further comprises step 162 of arming the first controller 30 (see FIGS. 2A, 4A). As discussed above and shown in FIG. 3B, arming the first controller 30 in the second position 132, or armed position, comprises turning on or activating the arm switch 114 (see FIGS. 2A, 4A) of the arm trigger switch 110 (see FIGS. 2A, 4A). This causes the impact element 22 (see FIG. 3B) and the elastically driven element 24 (see FIG. 3B) to be moved backwards. In this way, the portion 78 (see FIG. 3B) of the elastically driven element 24, which is preferably made of a metal material, contacts the magnetic tip portion 76 (see FIG. 3B) of the actuator element 26 (see FIG. 3B). The magnetic tip portion 76 (see FIG. 3B) of the actuator element 26 (see FIG. 3B) holds the portion 78 (see FIG. 3B) of the elastically driven element 24 (see FIG. 3B) in the second position 132 (see FIG. 3B), or armed position.

With step 162, the impact element 22 (see FIG. 3B) is not in contact with the test element 46 (see FIG. 3B), and the elastically driven element 24 (see FIG. 3B) is in contact with the actuating element 26 (see FIG. 3B). The actuating element 26 (see FIG. 3B) holds the elastically driven element 24 (see FIG. 3B) in place.

As shown in FIG. 5, the method 150 further comprises step 164 of triggering the first controller 30 (see FIGS. 2A, 4A) to initiate modal impact testing of the rotating test element 46 (see FIGS. 2A, 4A). As discussed above and shown in FIG. 3C, triggering the first controller 30 in the third position 134, or triggered position, comprises turning on or activating the trigger switch 116 (see FIGS. 2A, 4A) of the arm trigger switch 110 (see FIGS. 2A, 4A). This causes the actuating element 26 (see FIG. 3C), such as in the form of electromagnetic solenoid 26a (see FIG. 3C), to release the elongated body portion 62 (see FIG. 3C) of the elastically driven element 24 (see FIG. 3C), such as in the form of tuned-length leaf spring 24a (see FIG. 3C). This, in turn, causes the impact element 22 (see FIG. 3C), such as in the form of impact hammer 22a, and the elastically driven element 24 (see FIG. 3C), such as in the form of tuned-length leaf spring 24a (see FIG. 3C), to spring forward with a spring force toward the test element 46 (see FIG. 3C).

The tip portion 56 (see FIG. 3C) of the impact element 22 (see FIG. 3C) then impacts or contacts the portion 58 (see FIG. 3C) of the test element 46 (see FIG. 3C). As shown in FIG. 3C, in the third position 134, the impact element 22 is in contact with the test element 46, and the elastically driven element 24 is not in contact with the actuating element 26.

As shown in FIG. 5, the method 150 further comprises step 166 of obtaining with the data acquisition assembly 36 (see FIGS. 2A, 4A), data at different rotational speeds of the rotating test element 46. The data is obtained from the modal impact testing. As discussed above, the data acquisition assembly 36 (see FIGS. 2A, 4A) may preferably comprise one or more of a signal analyzer 38 (see FIGS. 2A, 4A), a computer 40 (see FIGS. 2A, 4A), a computer processor 42 (see FIGS. 2A, 4A), and a power supply 44 (see FIGS. 2A, 4A). The power supply 44 (see FIGS. 2A, 4A) preferably comprises an integrated electronics piezoelectric power supply or another suitable power supply.

As shown in FIG. 5, the method 150 may further comprise after the obtaining step 166, the step 168 of repeating one or more times both the step 164 of triggering the first controller 30 (see FIGS. 2A, 4A) to initiate testing of the rotating test element 46 (see FIGS. 2A, 4A) and the step 166 of obtaining with the data acquisition assembly 36 (see FIGS. 2A, 4A), data at different rotational speeds of the rotating test element 46. By repeating step 164 and step 166 as desired or as needed, a desired average rotational speed may be obtained. The modal impact testing with the impact element 22 (see FIGS. 2A, 4A), such as in the form of impact hammer 22a (see FIGS. 2A, 4A), preferably needs to be conducted at several points or locations on the test element 46 (see FIGS. 2A, 4A).

As shown in FIG. 5, the method 150 may further comprise after the repeating step 168 and the obtaining step 166, the step 170 of determining a range of operational speeds of the rotating test element 46 (see FIGS. 2A, 4A). Determining a range of operational speeds of the rotating test element 46 (see FIGS. 2A, 4A) may preferably be at speeds X to N (see FIG. 5). Determining a range of operational speeds and obtaining data may be achieved by setting the rotating test element 46 and/or rotating element 126 (see FIGS. 2A, 4A) at multiple discrete settings prior to initiating one or more strikes by the impact element 22 (see FIGS. 2A, 4A), such as the impact hammer 22a (see FIGS. 2A, 4A), and prior to data acquisition. Alternatively, determining a range of operational speeds and obtaining data may be achieved by continuously ramping the speed and initiating one or more strikes by the impact element 22 (see FIGS. 2A, 4A), such as the impact hammer 22a (see FIGS. 2A, 4A), and data acquisition at predetermined rpms (revolutions per minute). Alternatively, determining a range of operational speeds and obtaining data may be achieved by continuously ramping the speed and initiating one or more strikes by the impact element 22 (see FIGS. 2A, 4A), such as the impact hammer 22a (see FIGS. 2A, 4A), and data acquisition at random intervals (the rpms (revolutions per minute) may be determined by analysis of the data).

As shown in FIG. 5, step 170 may further comprise step 172 of changing the rotational speed of the rotating test element 46 (see FIGS. 2A, 4A) to the next desired speed. The step 170 of determining the range of operational speeds of the rotating test element 46 (see FIGS. 2A, 4A) preferably comprises determining operational in a range of from about 1000 rpm (revolutions per minute) to about 20,000 rpm (revolutions per minute), or another suitable rpm depending on the machining apparatus 128 (see FIG. 2B) used.

As shown in FIG. 5, the method 150 may further comprises step 174 of testing complete when all the desired impact data from the modal impact testing has been obtained. As shown in FIG. 5, the method 150 may further comprise step 176 of analyzing and/or processing the data from the modal impact testing with the data acquisition assembly 36 (see FIGS. 2A, 4A). The data from the modal impact testing is the data obtained by the data acquisition assembly 36 (see FIGS. 2A, 4A). The data may be analyzed and/or processed in order to define operating or cutting parameters of a cutting device of a machining apparatus 128 (see FIG. 2B), such as a known cutting machine.

The modal impact testing method 150 using the modal impact testing system 12 with the modal impact testing assembly 10, is preferably used to analyze the dynamics or characteristics of the machining apparatus 128 (see FIGS. 2B-2C and 4B). For example, every combination of test element 46 (substituted in place of a known cutting device); holding element 124 (see FIGS. 2A, 4A), such as tool holder 124a (see FIGS. 2A, 4A); and, rotating element 126 (see FIGS. 2B-2C, 4B), such as spindle 126a (see FIGS. 2B-2C, 4B), may be analyzed.

The modal impact testing method 150 using the modal impact testing system 12 with the modal impact testing assembly 10, is preferably used at different operating or cutting parameters. The operating or cutting parameters preferably comprise one or more of feed rate; rotational speed of the cutting device; orientation and depths of cut of the cutting device; number, spacing and geometric configuration of cutting elements of the cutting device; or other suitable operating or cutting parameters.

Figure 6:
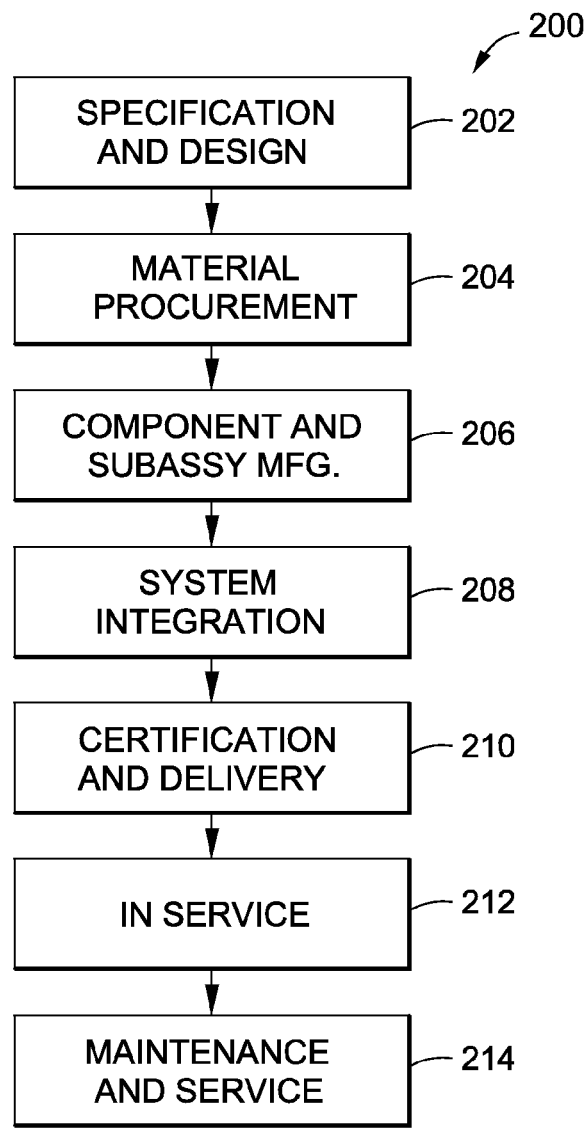
FIG. 6 is an illustration of a flow diagram of an embodiment of an aircraft manufacturing and service method of the disclosure; and, FIG. 7 is an illustration of a functional block diagram of an embodiment of an aircraft of the disclosure.
Figure 7:
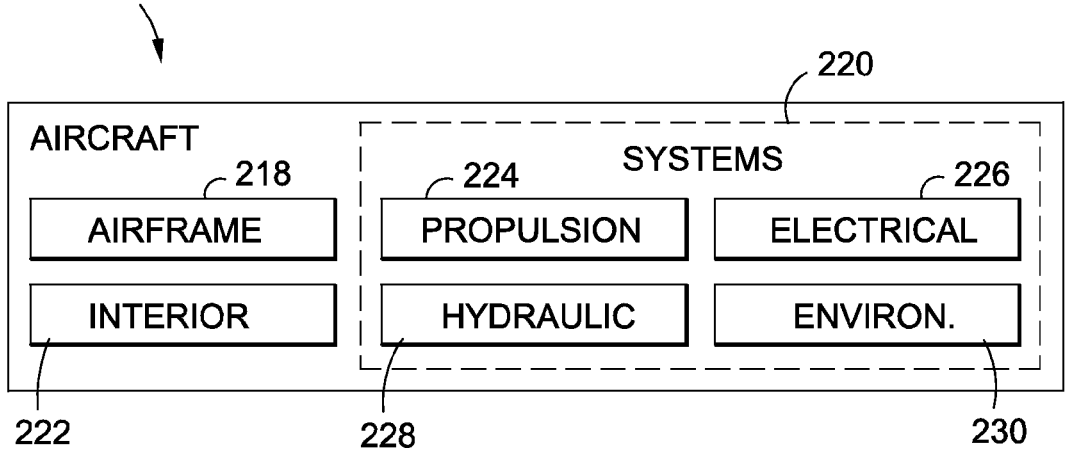

FIG. 6 is an illustration of a flow diagram of an aircraft manufacturing and service method 200. FIG. 7 is an illustration of a functional block diagram of an embodiment of an aircraft 216 of the disclosure. Referring to FIGS. 6-7, embodiments of the disclosure may be described in the context of the aircraft manufacturing and service method 200 as shown in FIG. 6, and the aircraft 216 as shown in FIG. 7.

During pre-production, exemplary aircraft manufacturing and service method 200 may include specification and design 202 of the aircraft 216 and material procurement 204. During manufacturing, component and subassembly manufacturing 206 and system integration 208 of the aircraft 216 takes place. Thereafter, the aircraft 216 may go through certification and delivery 210 in order to be placed in service 212. While in service 212 by a customer, the aircraft 216 may be scheduled for routine maintenance and service 214 (which may also include modification, reconfiguration, refurbishment, and other suitable services).

Each of the processes of the aircraft manufacturing and service method 200 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 7, the aircraft 216 produced by the exemplary aircraft manufacturing and service method 200 may include an airframe 218 with a plurality of systems 220 and an interior 222. Examples of the plurality of systems 220 may include one or more of a propulsion system 224, an electrical system 226, a hydraulic system 228, and an environmental system 230. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 200. For example, components or subassemblies corresponding to component and subassembly manufacturing 206 may be fabricated or manufactured in a manner similar to components or subassemblies produced while the aircraft 216 is in service 212. Also, one or more apparatus embodiments, method embodiments, or a combination thereof, may be utilized during component and subassembly manufacturing 206 and system integration 208, for example, by substantially expediting assembly of or reducing the cost of the aircraft 216. Similarly, one or more of apparatus embodiments, method embodiments, or a combination thereof, may be utilized while the aircraft 216 is in service 212, for example and without limitation, to maintenance and service 214.

Disclosed embodiments of the modal impact testing assembly 10 (see FIGS. 2A, 4A), modal impact testing system 12 (see FIGS. 2A, 4A), and modal impact testing method 150 (see FIG. 5) enable modal impact testing to be performed on test elements 46 (see FIGS. 2A, 4A) that are rotating at operational speeds, with no risk to the operator. The modal impact testing assembly 10 (see FIGS. 2A, 4A), modal impact testing system 12 (see FIGS. 2A, 4A), and modal impact testing method 150 (see FIG. 5) use a remotely-triggered excitation impulse from an impact hammer 22a (see FIGS. 2A, 4A) and a non-contact laser interferometer device 20a (see FIGS. 2A, 4A). The laser interferometer device 20a (see FIGS. 2A, 4A) serves as the element providing the response signal. This preferably needs to be done at several points on the test element 46 (see FIGS. 2A, 4A).

This, in turn, allows for prediction of accurate operational behavior and operating parameters of the machining apparatus 128 (see FIGS. 2B-2C) to be obtained, while the test element 46 (see FIGS. 2A, 4A) is rotating at operational speeds. The machining apparatus 128 (see FIGS. 2B-2C) may comprise a rotating cutting machine, such as may be used for machining a metallic fitting, or other machining tool device undergoing modal impact testing, Thus, the disclosed embodiments solve the problem of performing impact modal testing on a known rotating element, such as a rotating spindle, by substituting a test element 46, such as a test disc 46a (see FIGS. 2A, 4A) or a test bar 46b (see FIGS. 2A, 4A), for a known cutting device. The test element 46 preferably has a similar mass as the known cutting device. In addition, the impact modal testing is preferably performed within a non-accessible machine enclosure, such as a housing structure 48 (see FIGS. 2A, 4A).

Further, disclosed embodiments of the modal impact testing assembly 10 (see FIGS. 2A, 4A), modal impact testing system 12 (see FIGS. 2A, 4A), and modal impact testing method 150 (see FIG. 5) allow for analyzing of data obtained during testing of the test element 46, which replaces a known cutting device, while it is rotating. The data obtained during testing is preferably analyzed to determine the precise operational behavior of a rotating element 126 (see FIGS. 2B, 4B), such as a rotating spindle 126a (see FIGS. 2B, 4B) of a machining apparatus 128 (see FIGS. 2B-2C), prior to introduction into a manufacturing environment. This may eliminate months of experimental production required for machining equipment introduced into a manufacturing environment not having undergone such impact modal testing and analysis.

In addition, the disclosed embodiments of the modal impact testing assembly 10 (see FIGS. 2A, 4A), modal impact testing system 12 (see FIGS. 2A, 4A), and modal impact testing method 150 (see FIG. 5) do not require that an operator be in close proximity to the rotating element 126 (see FIG. 2A) and the test element 46 (see FIGS. 2A, 4A) when actuating the impact hammer 22a (see FIG. 2A). In addition, the disclosed embodiments do not require that connection elements, such as wires, be attached between the signal response measuring device 20 (see FIGS. 2A, 4A) and the test element 46 when the test element 46 rotates.

Moreover, the disclosed embodiments allow for modal impact testing of the test element 46 (see FIGS. 2A, 4A) attached to the rotating element 126 (see FIGS. 2A, 4A) of the machining apparatus 128 (see FIG. 2B), when the rotating element 126 is turned on. Further, the disclosed embodiments allow for obtaining data for impact modal analysis of rotating test elements 46, which replace known cutting devices, during the impact modal testing of the machining apparatus 128 (see FIGS. 2B, 4B). The disclosed embodiments also enable the determination of accurate operating parameters needed by machining apparatus programmers, such as machine tool programmers, without additional and costly trial-by-error analysis.

Further, the disclosed embodiments provide a stationary modal impact testing assembly 10a (see FIG. 2A) and a stationary modal impact testing system 12a (see FIG. 2A) that may be used, for example, in a machine testing center. Alternatively, the disclosed embodiments provide a portable modal impact testing assembly 10b (see FIG. 4A) and a portable modal impact testing system 12b (see FIG. 4A) that may be packaged into a portable unit capable of being used in the field.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. An assembly for modal impact testing, the assembly comprising:
    a first set of components comprising:
        an impact assembly;
        a cycle control element coupled to the impact assembly; and,
        a signal response measuring device comprising a laser interferometer device positioned opposite the impact assembly; and,
    a second set of components separate from the first set of components, the second set of components comprising:
        a first controller coupled to the cycle control element; and,
        a second controller comprising a laser interferometer controller coupled to the signal response measuring device comprising the laser interferometer device,
    the first set of components and the second set of components comprising a modal impact testing assembly for modal impact testing, the impact assembly of the modal impact testing assembly being configured to impact a test element rotating at operational speeds, the test element secured to a holding element that is attached to a rotating element configured to rotate the test element, the holding element securing the test element to be aligned between the impact assembly and the signal response measuring device.

2. The assembly of claim 1 wherein the modal impact testing assembly is a stationary modal impact testing assembly, and the first set of components and the test element are contained within a housing structure.

3. The assembly of claim 1 wherein the modal impact testing assembly is a portable modal impact testing assembly, and the first set of components are substantially contained within a housing structure.

4. The assembly of claim 1 wherein the impact assembly comprises:
    an impact element having a load cell configured to release an impact force output when the impact element impacts the test element;
    an elastically driven element attached to the impact element; and,
    an actuating element configured to actuate the impact element and the elastically driven element so that the impact element impacts the test element.

5. The assembly of claim 4 wherein the impact element comprises an impact hammer having a tip portion configured to impact a portion of the test element.

6. The assembly of claim 4 wherein the elastically driven element comprises a tuned-length leaf spring.

7. The assembly of claim 4 wherein the actuating element comprises an electromagnetic solenoid.

8. The assembly of claim 1 wherein the cycle control element comprises a trigger circuit device configured to trigger the impact assembly to impact the test element.

9. The assembly of claim 1 wherein the laser interferometer device is configured to measure a signal response when the impact assembly impacts the test element.

10. The assembly of claim 1 wherein the first controller comprises an arm trigger switch and a power element, the first controller configured to control and power the cycle control element, and the first controller coupled to the cycle control element either via a wired connection element or via a wireless connection.

11. The assembly of claim 1 wherein the laser interferometer controller is configured to control and power the signal response measuring device comprising the laser interferometer device, and is coupled to the signal response measuring device comprising the laser interferometer device either via a wired connection element or via a wireless connection.

12. A system for modal impact testing, the system comprising:
    a modal impact testing assembly comprising:
        a first set of components comprising:
            an impact assembly;
            a cycle control element coupled to the impact assembly; and,
            a signal response measuring device comprising a laser interferometer device positioned opposite the impact assembly; and,
        a second set of components separate from the first set of components, the second set of components comprising:
            a first controller coupled to the cycle control element of the modal impact testing assembly; and,
            a second controller comprising a laser interferometer controller coupled to the signal response measuring device comprising the laser interferometer device of the modal impact testing assembly,
    a test element secured to a holding element that is attached to a rotating element configured to rotate the test element, the holding element securing the test element for alignment between the impact assembly and the signal response measuring device, wherein the impact assembly of the modal impact testing assembly is configured to impact the test element while it is rotating at operational speeds; and, a data acquisition assembly coupled to the modal impact testing assembly, the modal impact testing assembly, the test element, and the data acquisition assembly together comprising a modal impact testing system for modal impact testing of the test element rotating at operational speeds.

13. The system of claim 12 wherein the modal impact testing system is a stationary modal impact testing system, and the first set of components and the test element are contained within a housing structure.

14. The system of claim 12 wherein the modal impact testing system is a portable modal impact testing system, and the first set of components are substantially contained within a housing structure.

15. The system of claim 12 wherein the impact assembly comprises:

an impact element having a load cell configured to release an impact force output when the impact element impacts the test element;

an elastically driven element attached to the impact element; and, an actuating element configured to actuate the impact element and the elastically driven element so that the impact element impacts the test element.

16. The system of claim 12 wherein the laser interferometer device is configured to measure a signal response when the impact assembly impacts the test element.

17. The system of claim 12 wherein the first controller comprises an arm trigger switch and a power element, and the first controller and the second controller are separately coupled to the modal impact testing assembly either via a wired connection element or via a wireless connection.

18. The system of claim 12 wherein the data acquisition assembly comprises one or more of a signal analyzer, a computer, a computer processor, and a power supply comprising an integrated electronics piezoelectric power supply, the data acquisition assembly coupled to the modal impact testing assembly either via one or more signal cable connection elements or via a wireless connection.

19. A method for modal impact testing, the method comprising the steps of:

securing a test element to a holding element and attaching the holding element to a rotating element configured to rotate the test element;

positioning the test element in relation to a modal impact testing assembly by aligning the test element between an impact assembly and a signal response measuring device of the modal impact testing assembly, the signal response measuring device comprising a laser interferometer device;

coupling a first controller to a cycle control element of the modal impact testing assembly;

coupling a second controller comprising a laser interferometer controller to the signal response measuring device comprising the laser interferometer device of the modal impact testing assembly;

coupling a data acquisition assembly to the first controller and to the second controller;

rotating the test element to determine an initial rotational speed;

arming the first controller;

triggering the first controller to initiate modal impact testing of the rotating test element; and, obtaining with the data acquisition assembly, data at different rotational speeds of the rotating test element.

20. The method of claim 19 further comprising after the obtaining step, the step of repeating one or more times both the step of triggering the first controller to initiate modal impact testing of the rotating test element and the step of obtaining with the data acquisition assembly, data at different rotational speeds of the rotating test element.

21. The method of claim 20 further comprising after the repeating step, the step of determining a range of operational speeds of the rotating test element and the step of analyzing the data with the data acquisition assembly in order to define operating or cutting parameters of a cutting device of a machining apparatus.

22. The method of claim 21 wherein the step of analyzing the data further comprises defining operating or cutting parameters comprising one or more of feed rate; rotational speed of the cutting device; orientation and depths of cut of the cutting device; and number, spacing and geometric configuration of cutting elements of the cutting device.

23. The method of claim 19 wherein aligning the test element between the impact assembly and the signal response measuring device comprising the laser interferometer device comprises aligning the test element between an impact hammer configured to impact the test element, and the laser interferometer device configured to measure a response signal from the test element after impact with the impact hammer.

24. The method of claim 19 wherein the step of positioning the test element in a modal impact testing assembly comprises positioning the test element in relation to either a stationary modal impact testing assembly or to a portable modal impact testing assembly.

25. The method of claim 19 wherein the step of coupling the data acquisition assembly to the first controller and to the second controller comprises coupling the data acquisition assembly comprising one or more of a signal analyzer, a computer, a computer processor, and a power supply, to the first controller and to the second controller either via one or more signal cable connection elements or via a wireless connection.

* * * * *